(12) United States Patent
Tsutsumi et al.

(10) Patent No.: US 6,790,973 B2
(45) Date of Patent: Sep. 14, 2004

(54) RUTHENIUM COMPLEXES AND PROCESS FOR PREPARING ALCOHOLIC COMPOUNDS USING THESE

(75) Inventors: Kunihiko Tsutsumi, Saitama (JP); Kunihiko Murata, Saitama (JP); Takeshi Ota, Saitama (JP); Takao Ikariya, Tokyo (JP)

(73) Assignee: Kanto Kagaku Kabushiki Kaisha, Tokyo (JP)

( * ) Notice: Subject to any disclaimer, the term of this patent is extended or adjusted under 35 U.S.C. 154(b) by 21 days.

(21) Appl. No.: 10/330,501

(22) Filed: Dec. 27, 2002

(65) Prior Publication Data

US 2003/0166978 A1 Sep. 4, 2003

(30) Foreign Application Priority Data

Dec. 28, 2001 (JP) .................... 2001-401170
Aug. 28, 2002 (JP) .................... 2002-248058

(51) Int. Cl.[7] .................. C07F 15/00; C07C 29/14
(52) U.S. Cl. ......................... 556/18; 568/881
(58) Field of Search ................. 556/18; 568/881

(56) References Cited

U.S. PATENT DOCUMENTS

5,614,641 A   3/1997   Genet et al. ............ 549/313
5,763,688 A   6/1998   Ikariya et al. ........... 568/814

FOREIGN PATENT DOCUMENTS

| JP | 08-225466 | 9/1996 |
| JP | 11-189600 | 7/1999 |
| JP | 2001-401157 | 12/2001 |
| WO | WO 01/74829 A1 | 10/2001 |

OTHER PUBLICATIONS

Akotsi et al., "Versatile precursor to ruthenium–bis (phosphine) hydrogenation catalysts", Database Accession No. 133:121957CA, XP002249784; Chirality (2000), 12 (5/6), p. 514–522.
Bianchini et al.,, "In situ and Reactor Study of the Enantioselective Hydrogenation of Acetylacetone by Ruthenium Catalysis with the New Chiral Diphosphine Ligand (R)–(R)–3–Benzyl–2,4–bis(diphenylphosphino)pentane", Organometallics (2000), 19(13), p. 2450–2461, XP002249778.
Steinmetz and Schenk, "Convenient Synthesis of [($\eta^5$–C$_5$Me$_5$)Ru(NCMe)$_3$]PF$_6$ and the Phosphine Derivatives [($\eta_5$–C$_5$Me$_5$)Ru(PR$_3$)$_2$(NCMe)]PF$_6$", Organometallics (1999), 18(5), p. 943–946, XP002249779.
Zanetti et al., "Synthesis, Characterization, and Application in Asymmetric Hydrogenation Reactions of Chiral Ruthenium(II) Diphosphine Complexes", Organometallics (1996), 15(2), p. 860–866, XP002249780.

Genet et al., "Enantioselective hydrogenation reactions with a full set of preformed and prepared in situ chiral diphosphine–ruthenium(II) catalysts", Tetrahedron: Asymmetry (1994), 5(4), p. 675–690, XP002249781.
Genetic et al., "Novel, general synthesis of the chiral catalysts diphosphine–ruthenium(II) diallyl complexes and a new practical in situ preparation of chiral ruthenium(II) catalysts", Tetrahedron: Asymmetry (1994), 5(4), p. 665–674, XP002249782.
Genet et al., "Asymmetric hydrogen transfer reaction of aryl ketoneswith chiral diphosphine–ruthenium(II) catalysts", Accession No. 120;133939 CA, Synlett (1993), 7, p. 478–80, XP002249785.
Manimaran et al., "In situ generation of ruthenium–chiral phosphine complexes and their use in asymmetric hydrogeneration", (1993), Organometallics 12(4), p. 1467–1470, XP002249783.

(List continued on next page.)

*Primary Examiner*—Porfirio Nazario-Gonzalez
(74) *Attorney, Agent, or Firm*—Wolf, Greenfield & Sacks, P.C.

(57) ABSTRACT

The invention provides novel ruthenium complexes having an optically active diphosphine compound, which has asymmetry on carbon and is easy to synthesize, as the ligand and a process for preparing optically active alcoholic compounds using said complexes as the catalysts, wherein said process is the process for preparing optically active alcoholic compounds, which are excellent in terms of reactivity, enatioselectivity and the like in an asymmetric hydrogenation of carbonyl compounds compared with conventional ruthenium complex catalysts having an optically active diphosphine compound having the axial chirality or the asymmetry on carbon as the ligand.

In a preferred embodiment, the invention provides an optically active ruthenium complex represented by the general formula (1)

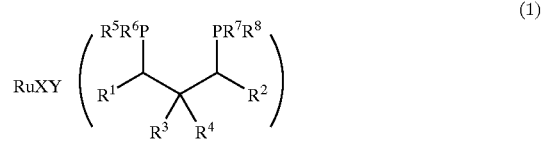

(1)

wherein X and Y, which can be identical to or different from each other, represent a hydrogen atom or an anion group, $R^1$ and $R^2$, which can be identical to or different from each other, represent a chain or cyclic hydrocarbon group of carbon number 1 to 20, which can be substituted, $R^3$ and $R^4$, which can be identical to or different from each other, represent a hydrogen atom or a hydrocarbon group of carbon number 1 to 3, and $R^5$, $R^6$, $R^7$ and $R^8$, which can be identical to or different from one another, represent a hydrocarbon group of carbon number 1 to 30, which can be substituted, with the proviso that when X and Y are bromine, $R^1$ and $R^2$ are a methyl group, and when $R^3$ and $R^4$ are a hydrogen atom, at least one of $R^5$, $R^6$, $R^7$ and $R^8$ is not a phenyl group.

15 Claims, No Drawings

OTHER PUBLICATIONS

Abel, E.W., et al., eds. Comprehensive Organometallic Chemistry II: A Review of the Literature 1982–1984: vol. 7:Iron, Ruthenium and Osmium. c. 1995 Pergamon Press, Elsevier Science Ltd. pp. 294–298.

Akotsi, O.W., et al., "Versatile precursor to Ruthenium–Bis(phosphine) hydrogenation catalysts." *Chirality.* 12:514–522 (2000).

Burk, M., et al., "A catalyst for efficient and highly enantioselective hydrogenation of aromatic heteroaromatic and ,–unsaturated ketones." *Organic Letters* (2000) 2(26):4173–4176.

Cai, D., et al., "Synthesis of chiral 2,2'–bis(diphenylphosphino)–1,1'–binaphthyl (BINAP) via a novel nickel–catalyzed phosphine insertion." *J. Org. Chem.* (1994) 59:7180–7181.

Cao, P., et al., "Ru–BICP–catalyzed asymmetric hydrogenation of aromatic ketones." *J. Org. Chem.* (1999) 64:2127–2129.

Cenini, S., et al., "Low oxidation states ruthenium chemistry VI. Stoichiometric and catalytic oxidation by molecular oxygen of primary amines bound to dichlorobis(triphenylphosphine)Ruthenium(II)." *J. Molecular Catalysis.* (1982) 15:297–308.

Doucet, et al., "Trans–RuCl$_2$(diphosphane)(1,2–diamine): shelf–stable precatalysts for the rapid, productive and stereoselective hydrogenation of ketones." *Angew. Chem. Int. Ed.* (1998) 37(12):1703–1707.

Hallman, P.S., et al., "Tetrakis(triphenylphosphine)dichlororuthenium(II) and tris(triphenylphosphine)–dichlororuthenium(II)." *Inorganic Synthesis* (1970) 12:237–240.

Kitamura, M., et al., "Homogeneous asymmetric hydrogenation of functionalized ketones." *J. Am. Chem. Soc.,* (1988) 110:629–631.

Ohkuma, T., et al., "Asymmetric hydrogenation of alkenyl, cycloproply, and aryl kentones, RuCl$_2$(xylbinap)(1,2–diamine) as a precatalyst exhibiting a wide scope." *J. Am. Chem. Soc.* (1998) 120:13529–13530.

Ohkuma, T., et al., "Practical Enantioselective hydrogenation of aromatic ketones" *J. Am. Chem. Soc.* (1995) 117:2675–2676.

Uozumi, Y., et al., "Synthesis of optically active 2–(Diarylphosphino)–1,1'–binaphthyls, efficient chiral monodentate phosphine ligands." *J. Org. Chem.* (1993) 58:1945–1948.

RUTHENIUM COMPLEXES AND PROCESS FOR PREPARING ALCOHOLIC COMPOUNDS USING THESE

FIELD OF THE INVENTION

The invention relates to a novel ruthenium complex and a process using said complex as a catalyst for preparing an optically active alcoholic compound. More particularly, the invention relates to a ruthenium complex, which is a highly efficient catalyst useful for preparing an optically active alcoholic compound as an intermediate or the like of pharmaceuticals, agricultural chemicals or commodity chemicals, and a process using said complex as a catalyst for preparing an optically active alcoholic compound.

BACKGROUND OF THE INVENTION

Transition metal complexes having optically active diphosphine compounds as the ligands are extremely useful as catalysts for asymmetric reactions and a large number of catalysts have been developed so far. Since the optically active diphosphine compounds give a great effect to a catalyst performance, a variety of optically active diphosphine compounds have been developed. For example, an axially chiral diphosphine compound represented by BINAP or a diphosphine compound having asymmetry on carbon such as DIOP are known. However, although asymmetric hydrogenation or asymmetric reduction catalysts, which have been examined in a large number, are useful as catalysts for olefins or carbonyl compounds having a functional group, they have not shown either a sufficient efficiency or a sufficient enatioselection for the reactions of carbonyl compounds having no functional group.

In order to solve these problems, optically active ruthenium metal complexes having as the ligand an axially chiral diphosphine compound and an optically active diamine compound have recently been developed and a highly efficient as well as highly stereoselective hydrogenation or reduction of carbonyl compounds have become possible. For example, as described in JP, A, 8-225466 and J. Am. Chem. Soc. 1995, 117, 2675, a process for carrying out the asymmetric hydrogenation of a carbonyl compound using a three-component catalyst system consisting of "ruthenium complex having as the ligand an optically active diphosphine compound", "optically active diamine compound" and "base" has been developed. Also, as described in JP, A, 11-189600, J. Am. Chem. Soc. 1998, 120, 13529 and Angew. Chem. Int. Ed. 1998, 37, 1703, a process for carrying out the asymmetric hydrogenation of a carbonyl compound using a two-component system catalyst consisting of "ruthenium complex having as the ligands a diphosphine compound and a vdiamine compound" and "base", improving complexity of the reaction using the three-component system has been reported.

In the above patents and reports, although the use of catalysts having as the ligand BINAPs (hereinafter BINAP, TolBINAP and XylBINAP generically are referred to as BINAPs) is reported, reporting examples of catalysts having as the ligands other axially chiral diphosphine compounds are not abundant. As for an example of the asymmetric hydrogenation of carbonyl compounds using a ruthenium metal complex having as the ligand an axially chiral diphosphine compound except BINAP, as described in WO 01/74829 and Org. Lett. 2000, 2, 26, 4173, catalysts consisting of two components of a ruthenium complex having as the ligands an optically active PHANEPHOS and an optically active diamine compound and a base have been reported. Further, in J. Org. Chem. 1999, 64, 2127, the asymmetric hydrogenation of carbonyl compounds using a three-component system catalyst consisting of a ruthenium complex having the optically active BICP as the ligand, an optically active diamine compound and a base has been reported. By the catalyst of WO 01/74829 and Org. Lett. 2000, 2, 26, 4173 the symmetric hydrogenation of acetophenone gives an optically active phenethyl alcohol of the optical purity 99% ee. The catalyst of J. Org. Chem. 1999, 64, 2127 gives an optically active phenethyl alcohol of the optical purity 76% ee by the asymmetric hydrogenation of acetophenone.

On the other hand, there are fewer examples of the asymmetric hydrogenation of carbonyl compounds by a ruthenium metal complex having an optically active diphosphine compound with asymmetry on carbon as the ligand, and an effective catalyst has not been found. For example, in CHIRALITY 2000, 12, 514 the asymmetric hydrogenation of acetophenone using a two-component system catalyst consisting of a ruthenium complex having the optically active SKEWPHOS and the optically active DPEN as the ligands and a base has been reported, achieving phenethyl alcohol of the optical purity 84% ee. In JP, A, 8-225466 one example of the symmetric hydrogenation of β-ionone using a catalyst consisting of three components of a ruthenium complex having the optically active CHIRAPHOS as the ligand, an optically active diamine compound and a base has been reported, and the corresponding optically active alcohol is obtained in the optical purity 53% ee. In both CHIRALITY 2000, 12, 514 and JP, A, 8-225466 the optical purity is lower compared with the case using a ruthenium complex having the above BINAPs as the ligand. Although in Angew. Chem. Int. Ed. 1998, 37, 1703 the synthesis of ruthenium complexes having the optically active DIOP or the optically active CHIRAPHOS as the ligand is reported, examination as a catalyst for the asymmetric hydrogenation of a carbonyl compound is not carried out.

As described above, since a catalyst consisting of a ruthenium metal complex having an axially chiral diphosphine compound represented by BINAPs and a chiral diamine compound as the ligand and a base enables the asymmetric hydrogenation of a wide range of carbonyl compounds and shows a high reactivity and a high enantioselectivity, giving an optically active alcohol with a high optical purity and therefore, it is of high utility value. However, since said catalyst does not necessarily show a high performance with respect to all the carbonyl compounds, development of a catalyst having an optically active diphosphine ligand other than BINAPs is desired.

Further, there are drawbacks in the synthesist of axially chiral diphosphine compounds. For example, the optically active BINAP is synthesized from binaphthol, which is obtained by the optical resolution, by methods shown in the following.

In J. Org. Chem. 1993, 58, 1945 the reaction of 2,2'-bis-(trifuluoromethanesulfonyl)oxy-1,1'-binaphthyl derivatized from the optically active binaphthol and in J. Org. Chem. 1994, 59, 7180 the synthesis by the reaction of 2,2'-bis-(trifuluoromethanesulfonyl)oxy-1,1'-binaphthyl and diphenylphosphine are reported.

However, the above synthetic methods require beforehand obtain the optically active binaphthol by the optical resolution from racemic binaphthol and further derivatize this optically active binaphthol to an optically active diphosphine compound of axial chirality.

As described above, in the process for obtaining axially chiral diphosphine compounds in many cases the steps are generally tedious since 1) the synthesis is multi-steps, 2) the optical resolution step is required.

As described above, with respect to the asymmetric hydrogenation by a three-component catalyst system consisting of a ruthenium complex having an optically active diphosphine compound with asymmetry on carbon as the ligand, an optically active diamine compound and a base, or by a two-component system catalyst consisting of a ruthenium complex having an optically active diphosphine compound with asymmetry on carbon and an optically active diamine compound as the ligands and a base, the reported examples are extremely few, and complexes satisfying a catalytic performance have not yet been developed.

SUMMARY OF THE INVENTION

Consequently, the invention solves the foregoing problems in the art and provides novel ruthenium complexes having an optically active diphosphine compound, which has asymmetry on carbon and is easy to synthesize, as the ligand and a process for preparing optically active alcoholic compounds using said complex as the catalyst, wherein said process is for preparing optically active alcoholic compounds, which are excellent in terms of reactivity, enatioselectivity and the like in an asymmetric hydrogenation of carbonyl compounds compared with conventional ruthenium complex catalysts having an optically active diphosphine compound having the axial chirality or the asymmetry on carbon as the ligand.

Diphosphine compounds having asymmetry on carbon can easily be synthesized without an optical resolution step or the like, and thus the inventors made extensive studies noting that they may become more effective over BINAPs if a higher performance of catalysts having them as the ligands is realized.

That is, based on that as an optically active diphosphine compound having asymmetry on carbon there is, for example, an optically active SKEWPHOS, the inventors noticed that said compound can easily be synthesized by the method described in Japanese Patent Application No. 2001-401157 using as the material optically active 2,4-pentanediol obtained from 2,4-pentanedione by the method described in J. Am. Chem. Soc. 1988, 110, 629 without an optical resolution, and synthesized a variety of novel ruthenium complexes having optically active SKEWPHOS derivatives as the ligands and made extensive studies on their performance as the asymmetric hydrogenation catalyst for carbonyl compounds.

As a result, the inventors found out surprisingly that a ruthenium complex catalyst having as the ligand an optically active SKEWPHOS derivative, which is an optically active diphosphine compound having asymmetry on carbon and can more easily be synthesized compared with an axially chiral diphosphine compound such as the optically active BINAP, has an excellent property as an asymmetric hydrogenation catalyst for carbonyl compounds and that the above problems are solved, thus accomplishing the invention.

Namely, the invention relates to an optically active ruthenium complex represented by the general formula (1)

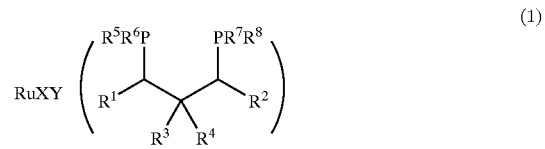

wherein X and Y, which can be identical to or different from each other, represent a hydrogen atom or an anion group, $R^1$ and $R^2$, which can be identical to or different from each other, represent a chain or cyclic hydrocarbon group of carbon number 1 to 20, which can be substituted, $R^3$ and $R^4$, which can be identical to or different from each other, represent a hydrogen atom or a hydrocarbon group of carbon number 1 to 3, and $R^5$, $R^6$, $R^7$ and $R^8$, which can be identical to or different from one another, represent a hydrocarbon group of carbon number 1 to 30, which can be substituted, with the proviso that when X and Y are bromine, $R^1$ and $R^2$ are a methyl group, and when $R^3$ and $R^4$ are a hydrogen atom, at least one of $R^5$, $R^6$, $R^7$ and $R^8$ is not a phenyl group.

Also, the invention relates to the above ruthenium complex wherein $R^1$ and $R^2$ are a methyl group, $R^3$ and $R^4$, which can be identical to or different from each other, are a hydrogen atom or a hydrocarbon group of carbon number 1 to 3, and $R^5$, $R^6$, $R^7$ and $R^8$, which can be identical to or different from one another, are a phenyl, 4-tolyl or 3,5-xylyl group.

Further, the invention relates to the above ruthenium complex wherein $R^1$ and $R^2$ are a methyl group, $R^3$ and $R^4$ are a hydrogen atom, and $R^5$, $R^6$, $R^7$ and $R^8$, which are identical to one another, are a 4-tolyl or 3,5-xylyl group.

Also, the invention relates to the above ruthenium complex wherein $R^1$ and $R^2$ are a phenyl group, $R^3$ and $R^4$, which can be identical to or different from each other, are a hydrogen atom or a hydrocarbon group of carbon number 1 to 3, and $R^5$, $R^6$, $R^7$ and $R^8$, which are identical to one another, are a phenyl, 4-tolyl or 3,5-xylyl group.

Further, the invention relates to the above ruthenium complex represented by the general formula (2)

wherein X and Y, which can be identical to or different from each other, represent a hydrogen atom or an anion group, and A is a compound represented by the below general formula (3)

wherein $R^1$ and $R^2$, which can be identical to or different from each other, represent a chain or cyclic hydrocarbon group of carbon number 1 to 20, which can be substituted, $R^3$ and $R^4$, which can be identical to or different from each other, represent a hydrogen atom or a hydrocarbon group of carbon number 1 to 3, and $R^5$, $R^6$, $R^7$ and $R^8$, which can be identical to or different from one another, represent a hydrocarbon group of carbon number 1 to 30, which can be substituted, and B is a compound represented by the below general formula (4)

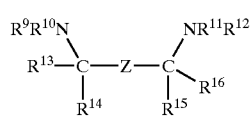
(4)

wherein $R^9$, $R^{10}$, $R^{11}$ and $R^{12}$, which can be identical to or different from one another, represent a hydrogen atom or a chain or cyclic hydrocarbon group of carbon number 1 to 30, which can be substituted, wherein at least one of these groups is a hydrogen atom, $R^{13}$, $R^{14}$, $R^{15}$ and $R^{16}$, which can be identical to or different from one another, represent a hydrogen atom or a chain or cyclic hydrocarbon group of carbon number 1 to 30, which can be substituted, and Z is a chain or cyclic hydrocarbon group of carbon number 1 to 10, which can be substituted, or a single bond.

Furthermore, the invention relates to the above ruthenium complex in which all of $R^5$, $R^6$, $R^7$ and $R^8$ are a phenyl group, wherein $R^{13}$ and $R^{15}$ are a hydrogen atom, $R^{14}$ and $R^{16}$ are a phenyl group, and when Z is a single bond, at least one of $R^9$, $R^{10}$, $R^{11}$ and $R^{12}$ is not a hydrogen atom.

And, the invention relates to the above ruthenium complex wherein all of $R^9$, $R^{10}$, $R^{11}$ and $R^{12}$ are a hydrogen atom, $R^{13}$ is a hydrogen atom, $R^{14}$ is an isopropyl group, $R^{15}$ and $R^{16}$ are 4-methoxyphenyl group, and Z is a single bond.

Also, the invention relates to the above ruthenium complex wherein the compound A is a TolSKEWPHOS: 2,4-bis-(di-4-tolylphosphino)pentane, a XylSKEWPHOS: 2,4-bis-(di-3,5-xylylphosphino)pentane, 2,4-bis-(diphenylphosphino)-3-methylpentane, 2,4-bis-(di-4-tolylphosphino)-3-methylpentane, 2,4-bis-(di-3,5-xylylphosphino)-3-methylpentane, 1,3-bis-(diphenylphosphino)-1,3-diphenylpropane, 1,3-bis-(di-4-tolylphosphino)-1,3-diphenylpropane, 1,3-bis-(di-3,5-xylylphosphino)-1,3-diphenylpropane, 1,3-bis-(diphenylphosphino)-1,3-diphenyl-2-methylpropane, 1,3-bis-(di-4-tolylphosphino)-1,3-diphenyl-2-methylpropane or 1,3-bis-(di-3,5-xylylphosphino)-1,3-diphenyl-2-methylpropane, and the compound B is diphenylethylenediamine or 1-isopropyl-2,2-di(p-methoxyphenyl) ethylenediamine.

Further, the invention relates to a process for preparing an alcoholic compound, wherein said process comprises a step of preparing the alcoholic compound by reducing a carbonyl compound with the reaction of hydrogen or a compound donating hydrogen in the presence of an optically active ruthenium complex represented by the general formula (1)

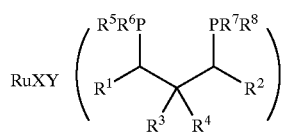
(1)

wherein X and Y, which can be identical to or different from each other, represent a hydrogen atom or an anion group, $R^1$ and $R^2$, which can be identical to or different from each other, represent a chain or cyclic hydrocarbon group of carbon number 1 to 20, which can be substituted, $R^3$ and $R^4$, which can be identical to or different from each other, represent a hydrogen atom or a hydrocarbon group of carbon number 1 to 3, and $R^5$, $R^6$, $R^7$ and $R^8$, which can be identical to or different from one another, represent a hydrocarbon group of carbon number 1 to 30, which an be substituted, with the proviso that when X and Y are bromine, $R^1$ and $R^2$ are a methyl group, and when $R^3$ and $R^4$ are a hydrogen atom, at least one of $R^5$, $R^6$, $R^7$ is $R^8$ does not represent a phenyl group, an optically active diamine compound represented by the general formula (4)

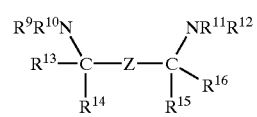
(4)

wherein $R^9$, $R^{10}$, $R^{11}$ and $R^{12}$ which can be identical to or different from one another, represent a hydrogen atom or a chain or cyclic hydrocarbon group of carbon number 1 to 30, which can be substituted, wherein at least one of these groups is a hydrogen atom, $R^{13}$, $R^{14}$, $R^{15}$ and $R^{16}$, which can be identical to or different from one another, represent a hydrogen atom or a chain or cyclic hydrocarbon group of carbon number 1 to 30, which can be substituted, and Z is a chain or cyclic hydrocarbon group of carbon number 1 to 10, which can be substituted, or a single bond, and a base (an alkaline metal or alkaline earth metal salt, or a quaternary ammonium salt).

Also, the invention relates to the above process, wherein $R^9$, $R^{10}$, $R^{11}$ and $R^{12}$ are a hydrogen atom, $R^{13}$ and $R^{15}$ are a hydrogen atom, $R^{14}$ and $R^{16}$ represent a phenyl group and Z represents a single bond, or $R^{13}$ represents a hydrogen atom, $R^{14}$ represents an isopropyl group, $R^{15}$ and $R^{16}$ represent 4-methoxyphenyl group and Z represents a single bond.

Further, the invention relates to the above process, wherein $R^1$ to $R^8$ are represented by the following a) to c):

a) $R^1$ and $R^2$ are a methyl group, $R^3$ and $R^4$, which can be identical to or different from each other, are a hydrogen atom or a hydrocarbon group of carbon number 1 to 3, and $R^5$, $R^6$, $R^7$ and $R^8$, which are one another identical, are a phenyl, 4-tolyl or 3,5-xylyl group;

b) $R^1$ and $R^2$ are a methyl group, $R^3$ and $R^4$ are a hydrogen atom, and $R^5$, $R^6$, $R^7$ and $R^8$, which are one another identical, are a 4-tolyl or 3,5-xylyl group; or c) $R^1$ and $R^2$ are a phenyl group, $R^3$ and $R^4$, which can be identical to or different from each other, represent a hydrogen atom or a hydrocarbon group of carbon number 1 to 3, and $R^5$, $R^6$, $R^7$ and $R^8$, which are one another identical, are a phenyl, 4-tolyl or 3,5-xylyl group.

Furthermore, the invention relates to a process for preparing an alcoholic compound, wherein said process comprises a step for preparing the alcoholic compound by reducing a carbonyl compound with the reaction of hydrogen or a compound donating hydrogen in the presence of an ruthenium complex represented by the general formula (2)

RuXYAB (2)

wherein X and Y, which can be identical to or different from each other, represent a hydrogen atom or an anion group, and A is a compound represented by the general formula (3)

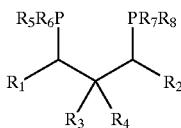 (3)

wherein $R^1$ and $R^2$, which can be identical to or different from each other, represent a chain or cyclic hydrocarbon group of carbon number 1 to 20, which can be substituted, $R^3$ and $R^4$, which can be identical to or different from each other, represent a hydrogen atom or a hydrocarbon group of carbon number 1 to 3, and $R^5$, $R^6$, $R^7$ and $R^8$, which can be identical to or different from one another, represent a hydrocarbon group of carbon number 1 to 30, which can be substituted, and B is a compound represented by the general formula (4)

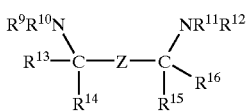 (4)

wherein $R^9$, $R^{10}$, $R^{11}$ and $R^{12}$, which can be identical to or different from one another, represent a hydrogen atom or a chain or cyclic hydrocarbon group of carbon number 1 to 30, which can be substituted, wherein at least one of these groups is a hydrogen atom, $R^{13}$, $R^{14}$, $R^{15}$ and $R^{16}$, which can be identical to or different from one another, represent a hydrogen atom or a chain or cyclic hydrocarbon group of carbon number 1 to 30, which can be substituted, and Z is a chain or cyclic hydrocarbon group of carbon number 1 to 10, which can be substituted, or a single bond, and a base (an alkaline metal or alkaline earth metal salt, or a quaternary ammonium salt).

The invention also relates to the above process, wherein $R^1$ to $R^{16}$, the compound A and the compound B are represented by either of the following a) to c):

a) all of $R^5$, $R^6$, $R^7$ and $R^8$ are a phenyl group (with the proviso that when $R^{13}$ and $R^{15}$ are a hydrogen atom, $R^{14}$ and $R^{16}$ are a phenyl group, and when Z is a single bond, at least one of $R^9$, $R^{10}$, $R^{11}$ and $R^{12}$ is not a hydrogen atom.);

b) all of $R^5$, $R^6$, $R^7$ and $R^8$ are a phenyl group, all of $R^9$, $R^{10}$, $R^{11}$ and $R^{12}$ are a hydrogen atom, $R^{13}$ is a hydrogen atom, additionally $R^{14}$ is an isopropyl group, $R^{15}$ and $R^{16}$ are a 4-methoxy-phenyl group and Z is a single bond, or c) The compound A is a TolSKEWPHOS: 2,4-bis-(di-4-tolylphosphino)pentane, a XylSKEWPHOS: 2,4-bis-(di-3,5-xylylphosphino)pentane, 2,4-bis-(diphenylphosphino)-3-methylpentane, 2,4-bis-(di-4-tolylphosphino)-3-methylpentane, 2,4-bis-(di-3,5-xylylphosphino)-3-methylpentane, 1,3-bis-(diphenylphosphino)-1,3-diphenylpropane, 1,3-bis-(di-4-tolylphosphino)-1,3-diphenylpropane, 1,3-bis-(di-3,5-xylylphosphino)-1,3-diphenylpropane, 1,3-bis-(diphenylphosphino)-1,3-diphenyl-2-methylpropane, 1,3-bis-(di-4-tolylphosphino)-1,3-diphenyl-2-methylpropane or 1,3-bis-(di-3,5-xylylphosphino)-1,3-diphenyl-2-methylpropane, and the compound B is diphenylethylenediamine or 1-isopropyl-2,2-di(p-methoxyphenyl)ethylenediamine.

Further, the invention relates to a process for preparing an optically active ruthenium complex represented by the general formula (1)

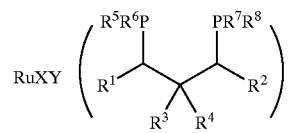 (1)

wherein X and Y, which can be identical to or different from each other, represent a hydrogen atom or an anion group, $R^1$ and $R^2$, which can be identical to or different from each other, represent a chain or cyclic hydrocarbon group of carbon number 1 to 20, which can be substituted, $R^3$ and $R^4$, which can be identical to or different from each other, represent a hydrogen atom or a hydrocarbon group of carbon number 1 to 3, and $R^5$, $R^6$, $R^7$ and $R^8$, which can be identical to or different from one another, represent a hydrocarbon group of carbon number 1 to 30, which can be substituted, with the proviso that when X and Y represent bromine, $R^1$ and $R^2$ are a methyl group, and when $R^3$ and $R^4$ are a hydrogen atom, at least one of $R^5$, $R^6$, $R^7$ and $R^8$ is not a phenyl group.), wherein said process comprises a step for obtaining the compound represented by the above general formula (1) by reacting a compound represented by the general formula (5)

RuXY (5)

wherein X and Y, which can be identical to or different from each other, represent a hydrogen atom or an anion group and a compound represented by the general formula (3)

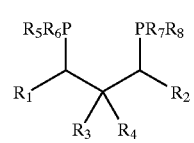 (3)

wherein $R^1$ and $R^2$, which can be identical to or different from each other, represent a chain or cyclic hydrocarbon group of carbon number 1 to 20, which can be substituted, $R^3$ and $R^4$, which can be identical to or different from each other, represent a hydrogen atom or a hydrocarbon group of carbon number 1 to 3, and $R^5$, $R^6$, $R^7$ and $R^8$, which can be identical to or different from one another, represent a hydrocarbon group of carbon number 1 to 30, which can be substituted.

Also, the invention relates to a process for preparing a ruthenium complex represented by the general formula (2)

RuXYAB (2)

wherein X and Y, which can be identical to or different from each other, represent a hydrogen atom or an anion group, A is a compound represented by the below general formula (3)

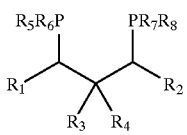
(3)

wherein $R^1$ and $R^2$, which can be identical to or different from each other, represent a chain or cyclic hydrocarbon group of carbon number 1 to 20, which can be substituted, $R^3$ and $R^4$, which can be identical to or different from each other, represent a hydrogen atom or a hydrocarbon group of carbon number 1 to 3, and $R^5$, $R^6$, $R^7$ and $R^8$, which can be identical to or different from one another, represent a hydrocarbon group of carbon number 1 to 30, which can be substituted.), and B is a compound represented by the general formula (4)

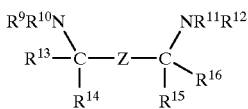
(4)

wherein $R^9$, $R^{10}$, $R^{11}$ and $R^{12}$, which can be identical to or different from one another, represent a hydrogen atom or a chain or cyclic hydrocarbon group of carbon number 1 to 30, which can be substituted, wherein at least one of these groups is a hydrogen atom, $R^{13}$, $R^{14}$, $R^{15}$ and $R^{16}$, which can be identical to or different from one another, represent a hydrogen atom or a chain or cyclic hydrocarbon group of carbon number 1 to 30, which can be substituted, and Z is a chain or cyclic hydrocarbon group of carbon number 1 to 10, which can be substituted, or a single bond, wherein said process comprises a step for obtaining the compound represented by the above general formula (2) by reacting a compound represented by the below general formula (1)

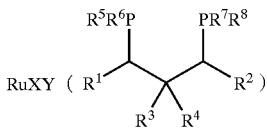
(1)

wherein each symbol has the same meaning as described above and the above compound B.

Axially chiral diphosphine compounds:

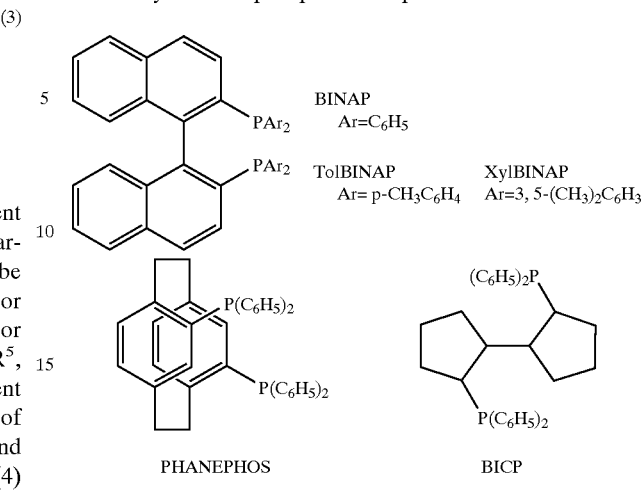

Diphosphine compounds having asymmetry on carbon:

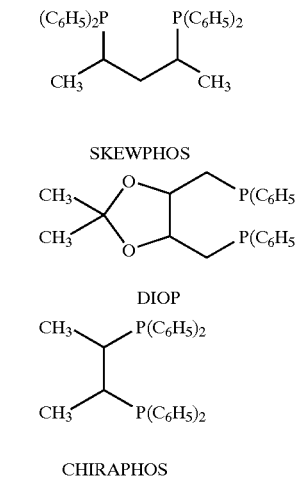

One example of the optically active diamine compounds is shown below.

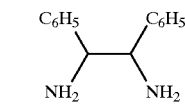

The meaning of abbreviation used here is as follows.

| | |
|---|---|
| BICP | Bis(diphenylphosphino)dicyclopentane |
| BINAP | 2,2'-bis(diphenylphosphino)-1,1'-binaphthyl |
| CHIRAPHOS | 2,3-bis(diphenylphosphino)butane |
| DIOP | 4,5-bis(diphenylphosphinomethyl)-2,2-dimethyl-1,3-dioxolane |
| DPEN | 1,2-diphenylethylenediamine |
| en | ethylenediamine |
| PHANEPHOS | 4,12-bis(diphenylphosphino)-[2.2]-paracyclophane |
| SKEWPHOS | 2,4-bis(diphenylphosphino)pentane |
| TolBINAP | 2,2'-bis(di-p-tolylphosphino)-1,1'-binaphthyl |

DETAILED DESCRIPTION OF THE PREFERRED EMBODIMENTS

The examples of the above mentioned axially chiral diphosphine compounds, the diphosphine compounds having asymmetry on a phosphorus atom and the diphosphine compounds having asymmetry on carbon, which are shown below.

| | -continued |
|---|---|
| XylBINAP | 2,2'-bis[bis(3,5-dimethylphenyl)phosphino]-1,1'-binaphthyl |

As above, the three components of the ruthenium complex shown in the general formula (1) which is used as the catalyst, the optically active diamine and the base, are indispensable components in order to make the asymmetric hydrogenation proceed smoothly and attain a high asymmetric yield, an optically active alcohol with a high optical purity not being obtained in a sufficient reaction activity even if one component is lacking.

Further, the invention also provides a process for preparing optically active alcoholic compounds by reducing carbonyl compounds with the reaction of hydrogen or a compound donating hydrogen in the presence of the ruthenium complex shown in the general formula (2) and the base (an alkaline metal or alkaline earth metal salt, or a quaternary ammonium salt).

As above, the two components of the ruthenium complex shown in the general formula (2) and the base, which is used as the catalyst, are indispensable components in order to make the asymmetric hydrogenation proceed smoothly and attain a high asymmetric yield, an optically active alcohol with a high optical purity not being obtained in a sufficient reaction activity even if one component is lacking.

Although the present invention has characteristics as described above, the mode for carrying out the invention is explained in more detail.

First, in the general formula (1)

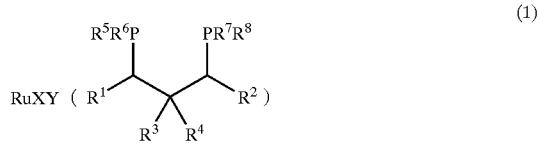

representing a ruthenium complex, X and Y, which can be identical to or different from each other, represent a hydrogen atom or an anion group. Although as said anion group a halogen atom or a carboxyl group is preferable, it may be any kind of other species, such as, for example, an alkoxy group, a hydroxyl group or the like. A hydrogen atom, a halogen atom or an acetoxyl group are preferable, with a halogen atom being particularly preferable.

Further, an optically active diphosphine compound in the optically active ruthenium complexes of the invention represented by the general formula (1) is shown by the following formula (3).

Here, $R^1$ and $R^2$, which can be identical to or different from each other, represent a chain or cyclic hydrocarbon group of carbon number 1 to 20, which can be substituted;, $R^3$ and $R^4$, which can be identical to or different from each other, represent a hydrogen atom or a hydrocarbon group of carbon number 1 to 3; and $R^5$, $R^6$, $R^7$ and $R^8$, which can be identical to or different from one another, represent a hydrocarbon group of carbon number 1 to 30, which can be substituted.

Here, $R^1$ and $R^2$ representing a chain or cyclic hydrocarbon group of carbon number 1 to 20 which can be substituted, can be a saturated or unsaturated hydrocarbon group, aliphatic or alicyclic, a monocyclic or polycyclic hydrocarbon group, aromatic or araliphatic or any species of these hydrocarbon groups having a substituent. Illustrative are, for example, hydrocarbon groups such as alkyl, alkenyl, cycloalkyl, cycloalkenyl, phenyl, naphthyl and phenylalkyl, and those having further each species of acceptable substituents such as alkyl, alkenyl, cycloalkyl, aryl, alkoxy, ester, acyloxy, halogen atoms, nitro group or cyano group on these hydrocarbon groups. Among these, methyl, ethyl, propyl, isopropyl groups and substituted or unsubstituted phenyl groups are preferable, with methyl and phenyl groups being particularly preferable.

Also, $R^3$ and $R^4$ representing a hydrogen atom or a hydrocarbon group of carbon number 1 to 3 are saturated aliphatic hydrocarbon groups. Specifically, preferable examples are methyl, ethyl, propyl or isopropyl group, etc.

Here, $R^5$, $R^6$, $R^7$ and $R^8$, which can be identical or different, representing a hydrocarbon group of carbon number 1 to 30 which can be substituted, can be a saturated or unsaturated hydrocarbon group aliphatic or alicyclic, a monocyclic or polycyclic hydrocarbon group aromatic or araliphatic or any species of these hydrocarbon groups having substituents. Illustrative are, for example, hydrocarbon groups such as alkyl, alkenyl, cycloalkyl, cycloalkenyl, phenyl, naphthyl and phenylalkyl and those having further any species of acceptable substituents such as alkyl, alkenyl, cycloalkyl, aryl, alkoxy, ester, acyloxy, halogen atoms, nitro group or cyano group on these hydrocarbon groups. Among these preferable are phenyl and substituted phenyl groups, a phenyl group and substituted phenyl group with one to five substituents of methyl, ethyl or propyl groups being particularly preferable.

Examples of the optically active diphosphine compounds represented by the general formula (3) include the following.

(1) Illustrative of pentane derivatives having diphenylphosphino group at the positions 2 and 4 are those of carbon number 1 to 3 at the position 3 or having no alkyl substituent such as SKEWPHOS having one or two alkyl substituents: 2,4-bis-(diphenylphosphino)pentane, 2,4-bis-(diphenylphosphino)-3-methylpentane, 2,4-bis-(diphenylphosphino)-3,3-dimethylpentane, 2,4-bis-(diphenylphosphino)-3-ethylpentane, 2,4-bis-(diphenylphosphino)-3,3-diethylpentane, 2,4-bis-(diphenylphosphino)-3-propylpentane, 2,4-bis-(diphenylphosphino)-3,3-dipropylpentane, 2,4-bis-(diphenylphosphino)-3-isopropylpentane, 2,4-bis-(diphenylphosphino)-3,3-diisopropylpentane, 2,4-bis-(diphenylphosphino)-3-ethyl-3-methylpentane, 2,4-bis-(diphenylphosphino)-3-methyl-3-propylpentane, 2,4-bis-(diphenylphosphino)-3-methyl-3-isopropylpentane, 2,4-bis-(diphenylphosphino)-3-ethyl-3-propylpentane, 2,4-bis-(diphenylphosphino)-3-ethyl-3-isopropylpentane, 2,4-bis-(diphenylphosphino)-3-propyl-3-isopropylpentane, etc.

(2) Illustrative of pentane derivatives having di-4-triphenylphosphino group at the positions 2 and 4 are those having one or two alkyl substituents of carbon number 1 to 3 at the position 3 or having no alkyl substituent such as TolSKEWPHOS: 2,4-bis-(di-4-triphenylphosphino)pentane, 2,4-bis-(di-4-triphenylphosphino)-3-methylpentane, 2,4-bis-(di-4-triphenylphosphino)-3,3-dimethylpentane, 2,4-bis-(di-4-triphenylphosphino)-3-ethylpentane, 2,4-bis-(di-4-triphenylphosphino)-3,3-diethylpentane, 2,4-bis-(di-4-triphenylphosphino)-3-propylpentane, 2,4-bis-(di-4-triphenylphosphino)-3,3- dipropylpentane, 2,4-bis-(di-4-triphenylphosphino)-3-isopropylpentane, 2,4-bis-(di-4-triphenylphosphino)-3,3-diisopropylpent 2,4-bis-(di-4-triphenylphosphino)-3-ethyl-3-methylpentane, 2,4-bis-(di-4-triphenylphosphino)-3-methyl-3-propylpentane, 2,4-bis-(di-4-triphenylphosphino)-3-methyl-3-isopropylpentane, 2,4-bis-(di-4-triphenylphosphino)-3-ethyl-3-propylpentane, 2,4-bis-(di-4-triphenylphosphino)-3-ethyl-3-isopropylpentane, 2,4-bis-(di-4-triphenylphosphino)-3-propyl-3-isopropylpentane, etc.

(3) Illustrative of pentane derivatives having di-3,5-xylylphosphino group at the positions 2 and 4 are those having one or two alkyl substituents of carbon number 1 to 3 at the position 3 or having no alkyl substituent such as XylSKEWPHOS: 2,4-bis-(di-3,5-xylylphosphino)pentane, 2,4-bis-(di-3,5-xylylphosphino)-3-methylpentane, 2,4-bis-(di-3,5-xylylphosphino)-3,3-dimethylpentane, 2,4-bis-(di-3,5-xylylphosphino)-3-ethylpentane, 2,4-bis-(di-3,5-xylylphosphino)-3,3-diethylpentane, 2,4-bis-(di-3,5-xylylphosphino )-3-propylpentane, 2,4-bis-(di-3,5-xylylphosphino)-3,3-dipropylpentane, 2,4-bis-(di-3,5-xylylphosphino)-3-isopropylpentane, 2,4-bis-(di-3,5-xylylphosphino)-3,3-diisopropylpentane, 2,4-bis-(di-3,5-xylylphosphino)-3-ethyl-3-methylpentane, 2,4-bis-(di-3,5-xylylphosphino)-3-methyl-3-propylpentane, 2,4-bis-(di-3,5-xylylphosphino)-3-methyl-3-isopropylpentane, 2,4-bis-(di-3,5-xylylphosphino)-3-ethyl-3-propylpentane, 2,4-bis-(di-3,5-xylylphosphino)-3-ethyl-3-isopropylpentane, 2,4-bis-(di-3,5-xylylphosphino)-3-propyl-3-isopropylpentane, etc.

(4) Illustrative of 1,3-diphenylpropane derivatives having diphenylphosphino group at the positions 1 and 3 are those having one or two alkyl substituents of carbon number 1 to 3 at the position 2, such as 1,3-bis-(diphenylphosphino)-1,3-diphenyl-2-methylpropane, 1,3-bis-(diphenylphosphino)-1,3-diphenyl-2,2-dimethylpropane, 1,3-bis-(diphenylphosphino)-1,3-diphenyl-2-ethylpropane, 1,3-bis-(diphenylphosphino)-1,3-diphenyl-2,2-diethylpropane, 1,3-bis-(diphenylphosphino)-1,3-diphenyl-2-propylpropane, 1,3-bis-(diphenylphosphino)-1,3-diphenyl-2,2-dipropylpropane, 1,3-bis-(diphenylphosphino)-1,3-diphenyl-2-isopropylpropane, 1,3-bis-(diphenylphosphino)-1,3-diphenyl-2,2-diisopropylpropane, 1,3-bis-(diphenylphosphino)-1,3-diphenyl -2-ethyl-2-methylpropane, 1,3-bis-(diphenylphosphino)-1,3-diphenyl-2-methyl-2-propylpropane, 1,3-bis-(diphenylphosphino)-1,3-diphenyl-2-methyl-2-isopropylpropane, 1,3-bis-(diphenylphosphino)-1,3-diphenyl-2-ethyl-2-propylpropane, 1,3-bis-(diphenylphosphino)-1,3-diphenyl-2-ethyl-2-isopropylpropane, 1,3-bis-(diphenylphosphino)-1,3-diphenyl-2-propyl-2-isopropylpropane, etc.

(5) Illustrative of 1,3-diphenylpropane derivatives having di-4-triphenylphosphino group at the positions 1 and 3 are those having one or two alkyl substituents of carbon number 1 to 3 at the position 2 or having no alkyl substituent, such as 1,3-bis-(di-4-tolylphosphino)-1,3-diphenylpropane, 1,3-bis-(di-4-tolylphosphino)-1,3-diphenyl-2-methylpropane, 1,3-bis-(di-4-tolylphosphino)-1,3-diphenyl-2,2-dimethylpropane, 1,3-bis-(di-4-tolylphosphino)-1,3-diphenyl-2-ethylpropane, 1,3-bis-(di-4-tolylphosphino)-1,3-diphenyl-2,2-diethylpropane, 1,3-bis-(di-4-tolylphosphino)-1,3-diphenyl-2-propylpropane, 1,3-bis-(diphenylphosphino)-1,3-diphenyl-2,2-dipropylpropane, 1,3-bis-(di-4-tolylphosphino)-1,3-diphenyl-2-isopropylpropane, 1,3-bis-(di-4-tolylphosphino)-1,3-diphenyl-2,2-diisopropylpropane, 1,3-bis-(di-4-tolylphosphino)-1,3-diphenyl-2-ethyl-2-methylpropane, 1,3-bis-(di-4-tolylphosphino)-1,3-diphenyl-2-methyl-2-propylpropane, 1,3-bis-(di-4-tolylphosphino)-1,3-diphenyl-2-methyl-2-isopropylpropane, 1,3-bis-(di-4-tolylphosphino)-1,3-diphenyl-2-ethyl-2-propylpropane, 1,3-bis-(di-4-tolylphosphino)-1,3-diphenyl-2-ethyl-2-isopropylpropane, 1,3-bis-(di-4-tolylphosphino)-1,3-diphenyl-2-propyl-2-isopropylpropane, etc.

(6) Illustrative of 1,3-diphenylpropane derivatives having di-3,5-xylylphosphino group at the positions 1 and 3 are those having one or two alkyl substituents of carbon number 1 to 3 at the position 2 or those having no alkyl substituent such as 1,3-bis-(di-3,5-xylylphosphino)-1,3-diphenylpropane, 1,3-bis-(di-3,5-xylylphosphino)-1,3-diphenyl-2-methylpropane, 1,3-bis-(di-3,5-xylylphosphino)-1,3-diphenyl-2,2-dimethylpropane, 1,3-bis-(di-3,5-xylylphosphino)-1,3-diphenyl-2-ethylpropane, 1,3-bis-(di-3,5-xylylphosphino)-1,3-diphenyl-2,2-diethylpropane, 1,3-bis-(di-3,5-xylylphosphino)-1,3-diphenyl-2-propylpropane, 1,3-bis-(di-3,5-xylylphosphino)-1,3-diphenyl-2,2-dipropylpropane, 1,3-bis-(di-3,5-xylylphosphino)-1,3-diphenyl-2-isopropylpropane, 1,3-bis-(di-3,5-xylylphosphino)-1,3-diphenyl-2,2-diisopropylpropane, 1,3-bis-(di-3,5-xylylphosphino)-1,3-diphenyl-2-ethyl-2-methylpropane, 1,3-bis-(di-3,5-xylylphosphino)-1,3-diphenyl-2-methyl-2-propylpropane, 1,3-bis-(di-3,5-xylylphosphino)-1,3-diphenyl-2-methyl-2-isopropylpropane, 1,3-bis-(di-3,5-xylylphosphino)-1,3-diphenyl-2-methyl-2-propylpropane, 1,3-bis-(di-3,5-xylylphosphino)-1,3-diphenyl-2-ethyl-2-isopropylpropane, 1,3-bis-(di-3,5-xylylphosphino)-1,3-diphenyl-2-propyl-2-isopropylpropane, etc.

SKEWPHOS, TolSKEWPHOSand XylSKEWPHOS are particularly preferable. However,of course, optically active diphosphine compounds which can be used in the invention are not in any way limited thereto.

The optically active ruthenium complex represented by the general formula (1) in some cases contains one or more organic compound which is a reagent. Here, the organic compounds are coordinate solvents, such as, for example, an aromatic hydrocarbon such as toluene or xylene, an aliphatic hydrocarbon such as pentane or hexane, a halogen containing hydrocarbon such as methylene chloride, an ether type solvent such as ether or tetrahydrofuran, an alcohol type solvent such as methanol, ethanol, 2-propanol, butanol or benzyl alcohol, a ketone type solvent such as acetone, methyl ethyl ketone, an organic solvent having a hetero atom such as acetonitrile, DMF (dimethylformamide), N-methyl pyrrolidone, DMSO (dimethyl sulfoxide) or triethylamine.

Further, although the general formula (2)

RuXYAB (2)

representing the ruthenium complex of the present invention has an optically active diphosphine compound represented by the general formula (3)

(3)

and an optically active diamine compound represented by the general formula (4),

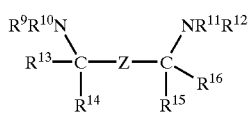

(4)

the substituents X,Y and the optically active diphosphine compound can appropriately be selected from a similar one to those in the general formula (1).

In the optically active diamine compounds of the optically active ruthenium complexes represented by the general formula (2), $R^9$, $R^{10}$, $R^{11}$ and $R^{12}$, which can be identical to or different from one another, represent a hydrogen atom or a chain or cyclic hydrocarbon group of carbon number 1 to 30, which can be substituted, wherein at least one of these groups is a hydrogen atom, and $R^{13}$, $R^{14}$, $R^{15}$ and $R^{16}$, which can be identical to or different from one another, represent a hydrogen atom or a chain or cyclic hydrocarbon group of carbon number 1 to 30, which can be substituted, and Z is a chain or cyclic hydrocarbon group of carbon number 1 to 10, which can be substituted or a single bond. Here, $R^9$, $R^{10}$, $R^{11}$ and $R^{12}$ representing at least one hydrogen atom as described above or a chain or cyclic hydrocarbon group of carbon number 1 to 30, which can be substituted, can be a hydrogen atom, a saturated or unsaturated hydrocarbon group aliphatic or alicyclic, a monocyclic or polycyclic hydrocarbon group aromatic or araliphatic or each species of these hydrocarbon groups having a substituent.

Illustrative are, for example, a hydrogen atom, hydrocarbon groups such as alkyl, alkenyl, cycloalkyl, cycloalkenyl, phenyl, naphthyl and phenylalkyl, and those having further any species of acceptable substituents such as alkyl, alkenyl, cycloalkyl, aryl, alkoxy, ester, acyloky, halogen atom, nitro group or cyano group on these hydrocarbon groups.

Among these preferably $R^9$ and $R^{11}$ are hydrogen atoms, $R^{10}$ and $R^{12}$ are alkyl, phenyl and phenylalkyl groups, and in particular preferably all are hydrogen atoms. Here, $R^{13}$, $R^{14}$, $R^{15}$ and $R^{16}$ as described above representing a hydrogen atom or a chain or cyclic hydrocarbon group of carbon number 1 to 30, which can be substituted, can be a hydrogen atom, a saturated or unsaturated hydrocarbon group aliphatic or alicyclic, a monocyclic or polycyclic hydrocarbon group aromatic or araliphatic or any species of these hydrocarbon groups having a substituents.

Illustrative are, for example, hydrocarbon groups such as alkyl, alkenyl, cycloalkyl, cycloalkenyl, phenyl, naphthyl and phenylalkyl, and those having further any species of acceptable substituents such as alkyl, alkenyl, cycloalkyl, aryl, alkoxy, ester, acyloxy, halogen atoms, nitro group or cyano group on these hydrocarbon groups. Among these preferable are a hydrogen atom, methyl, ethyl, propyl, isopropyl and substituted phenyl groups, with a hydrogen atom, isopropyl, phenyl and 4-methoxyphenyl groups being particularly preferable.

Also, illustrative of the optically active diamine compounds represented by the general formula (4)

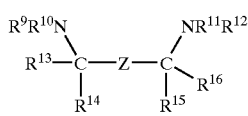

(4)

are DPEN: 1,2-diphenylethylenediamine, 1,2-cyclohexanediamine, 1,2-cyclobutanediamine, 2,3-dimethylbutanediamine, 1-methyl-2,2-diphenylethylenediamine, 1-isobutyl-2,2-diphenylethylenediamine, 1-isopropyl-2,2-diphenylethylenediamine, 1-methyl-2,2-di(p-methoxyphenyl)ethylenediamine, 1-isobutyl-2,2-di(p-methoxyphenyl)ethylenediamine, DAIPEN: 1-isopropyl-2,2-di(p-methoxyphenyl) ethylenediamine, 1-benzyl-2,2-di(p-methoxyphenyl) ethylenediamine, 1-methyl-2,2-dinaphthylethylenediamine, 1-isobutyl-2,2-dinaphthylethylenediamine, 1-isopropyl-2,2-dinaphthylethylenediamine, etc. In particular, DPEN and DAIPEN are preferable.

Further, the optically active diamine compounds are not limited to the illustrated optically active diamine compounds, and optically active derivatives of propandiamine, butanediamine, phenylenediamine, cyclohexanediamine derivatives and the like can be used.

The synthesis of the optically active ruthenium complexes represented by the general formula (1) can be carried out by reacting an optically active diphosphine compound and a starting ruthenium complex. Further, the synthesis of the ruthenium complexes represented by the general formula (2) can be carried out by reacting the optically active ruthenium complexes represented by the general formula (1) and an optically active diamine compound.

As the starting ruthenium complexes for the complex synthesis, ruthenium complexes of zero valency, monovalency, divalency, trivalency and a higher valency can be used. In case of using ruthenium complexes of zero valency or monovalency, oxidation of the ruthenium complexes before the final step is necessary. In case of divalent ruthenium complexes, the complexes can be synthesized by reacting a ruthenium complex and an optically active diphosphine compound, and an optically active diamine compound one after another, or in the reverse order, or simultaneously. In case of using trivalent and tetravalent ruthenium complexes, reduction of ruthenium is necessary before the final step.

As a starting ruthenium complex can be used an inorganic ruthenium compound such as ruthenium chloride (III) hydrate, ruthenium bromide (III) hydrate or ruthenium iodide (III) hydrate, a ruthenium compound coordinated with a diene such as [ruthenium dichloride (norbornadiene)] polynuclear complex, [ruthenium dichloride (cycloocta-1,5-diene)] polynuclear complex or bis(methylallyl)ruthenium (cycloocta-1,5-diene) polynuclear complex, a ruthenium compound coordinated with an aromatic compound such as [ruthenium dichloride (benzene)] polynuclear complex, [ruthenium dichloride (p-cymene)] polynuclear complex, [ruthenium dichloride (trimethylbenzene)] polynuclear complex or [ruthenium dichloride (hexamethylbenzene)] polynuclear complex, or a complex coordinated with phosphine such as dichlorotris(triphenylphosphine) ruthenium. Additionally, if it is a ruthenium complex having a ligand replaceable with optically active diphosphine compounds or the optically active diamine compounds, it is not limited to those described above. For example, a variety of ruthenium complexes shown in COMPREHENSIVE ORGANOMETALLIC CHEMISTRY II Vol 7, p. 294–296 (Pergamon) can be used as a starting material.

In case of using a trivalent ruthenium complex as a starting material, for example, a phosphine-ruthenium halide complex can be synthesized by reacting ruthenium halide (III) with an excess phosphine. Subsequently, by reacting the obtained phosphine-ruthenium halide complex with an amine the targeted amine-phosphine-ruthenium halide complex can be obtained. For example, regarding this synthesis, only one example is described in the literature [J. Mol. Cat., 15, 297 (1982)].

Namely, RuCl$_2$(PPh$_3$) synthesized by the method described in Inorg. Synth., Vol. 12, 237 (1970) is reacted with ethylenediamine in benzene to obtain RuCl$_2$(PPh$_3$)$_2$(en ethylenediamine) (with no description on the yield). Further, in this method the reaction is an inhomogenous system with a tendency that the starting material tends to remain unreacted. In the meantime, in case of changing the reaction solvent to a solvent such as methylene chloride or chloroform, the reaction can be carried out in a homogeneous condition to improve the operability.

The reaction of the ruthenium halide and the phosphine ligand is carried out in an aromatic hydrocarbon solvent such as toluene or xylene, an aliphatic hydrocarbon solvent such as pentane or hexane, a halogen-containing organic hydrocarbon solvent such as methylene chloride, an ether type solvent such as ether or tetrahydrofuran, an alcohol type solvent such as methanol, ethanol, 2-propanol, butanol or benzyl alcohol, a ketone type solvent such as acetone, methyl ethyl ketone, an organic solvent having a hetero atoms such as acetonitrile, DMF, N-methyl pyrrolidone or DMSO at a reaction temperature of between –100° C. and 200° C. to obtain an amine-phosphine-ruthenium halide complex.

The reaction of the obtained amine-phosphine-ruthenium halide complex with an amine ligand is carried out in an aromatic hydrocarbon solvent such as toluene or xylene, an aliphatic hydrocarbon solvent such as pentane or hexane, a halogen-containing organic hydrocarbon solvent such as methylene chloride, an ether type solvent such as ether or tetrahydrofuran, an alcohol type solvent such as methanol, ethanol, 2-propanol, butanol or benzyl alcohol, a ketone type solvent such as acetone, methyl ethyl ketone, an organic solvent having a hetero atoms such as acetonitrile, DMF, N-methyl pyrrolidone or DMSO at a reaction temperature of between –100° C. and 200° C. to obtain an amine-phosphine-ruthenium halide complex.

On the other hand, using a divalent ruthenium complex is used from the beginning, a reaction method in which this complex and a phosphine compound, and an amine compound are reacted one after another, or in the reverse order, or simultaneously. As an example, a ruthenium compound coordinated with a diene such as [ruthenium dichloride (norbornadiene)] polynuclear complex, [ruthenium dichloride (cycloocta-1,5-diene)] polynuclear complex or bis (methylallyl)ruthenium(cycloocta-1,5-diene) polynuclear complex, a ruthenium compound coordinated with an aromatic compound such as [ruthenium dichloride (benzene)] dinuclear complex, [ruthenium dichloride (p-cymene)] dinuclear complex, [ruthenium dichloride (trimethylbenzene)] dinuclear complex or [ruthenium dichloride (hexamethylbenzene)] dinuclear complex, or a complex coordinated with phosphine such as dichlorotris (triphenylphosphine) ruthenium is reacted with the phosphine compound in an aromatic hydrocarbon solvent such as toluene or xylene, an aliphatic hydrocarbon solvent such as pentane or hexane, a halogen-containing organic solvent hydrocarbon solvent such as methylene chloride, an ether type solvent such as ether or tetrahydrofuran, an alcohol type solvent such as methanol, ethanol, 2-propanol, butanol or benzyl alcohol, a ketone type solvent such as acetone, methyl ethyl ketone, an organic solvent having a hetero atoms such as acetonitrile, DMF, N-methyl pyrrolidone or DMSO at a reaction temperature of between –100° C. and 200° C. to obtain a phosphine-ruthenium-methylallyl complex.

The reaction of the obtained phosphine-ruthenium halide complex with the amine compound is carried out in an aromatic hydrocarbon solvent such as toluene or xylene, an aliphatic hydrocarbon solvent such as pentane or hexane, a halogen-containing organic hydrocarbon solvent such as methylene chloride, an ether type solvent such as ether or tetrahydrofuran, an alcohol type solvent such as methanol, ethanol, 2-propanol, butanol or benzyl alcohol, a ketone type solvent such as acetone, methyl ethyl ketone, an organic solvent having a hetero atoms such as acetonitrile, DMF, N-methyl pyrrolidone or DMSO at a reaction temperature of between –100° C. and 200° C. to obtain an amine-phosphine-ruthenium halide complex. Also under a similar condition, by reacting a cationic ruthenium complex such as [chlororuthenium (BINAP)(benzen)]chloride, with an amine complex, an amine-phosphine-ruthenium halide complex can be obtained.

For example, in case of using a ruthenium complex synthesized as above represented by the general formula (1) or the general formula (2), although the amount used varies depending on a reaction vessel or economies, the range of 1/100 to 1/1,000,000, preferably 1/500 to 1/1,000,000, based on the carbonyl compound, which is a reaction substrate, can be used.

An optically active ruthenium complex represented in the general formula (1), when X and Y are a hydrogen atom, is mixed with a carbonyl compound without addition of a base after addition of an optically active diamine compound, and the mixture is stirred under the pressurized hydrogen or in the presence of a hydrogen donating material. Thus, hydrogenation of the carbonyl compound can be carried out. In case of using excess carbonyl compound against the catalyst there is a desirable case in which a base is added. In the meantime in case of X and Y representing a group except a hydrogen atom it is also effective after adding a base and an optically active diamine compound a carbonyl compound is mixed, and to stir the mixture under the pressurized hydrogen or the presence of a hydrogen donating material to carry out hydrogenation of the carbonyl compound.

As above, the three components of the ruthenium complex shown in the general formula (1) which is used as a catalyst, the optically active diamine of the general formula (4) and the base are indispensable components in order to make the asymmetric hydrogenation proceed smoothly and attain a high asymmetric yield, and an optically active alcohol with a high optical purity can not be obtained in a sufficient reaction activity even if one component is lacking. The amount used of the optically active diamine ligand used here is 0.5–2.5 equivalents, preferably 1–2 equivalents against the ruthenium complex.

An optically active ruthenium complex represented in the general formula (2), when X and Y are a hydrogen atom, without addition of a base after addition of a carbonyl compound, the mixture is stirred under the pressurized hydrogen or in the presence of a hydrogen donating material. Thus, hydrogenation of the carbonyl compound can be carried out. In case of using excess carbonyl compound against the catalyst there is a desirable case in which a base is added. On the other hand, in case of X and Y represent a group except a hydrogen atom it is also effective after mixing with a carbonyl compound under the presence of a base, to pressurize hydrogen or to stir the mixture under the presence of a hydrogen donating material to carry out hydrogenation of the carbonyl compound.

As above, the two components of the optically active ruthenium complex shown in the general formula (2) which is used as a catalyst and the base are indispensable components in order to make the asymmetric hydrogenation proceed smoothly and attain a high asymmetric yield, and an optically active alcohol with a high optical purity can not be obtained in a sufficient reaction activity even if one component is lacking.

Also, with respect to the bases used in the invention, alkaline metal salts such as KOH, KOCH$_3$, KOCH(CH$_3$)$_2$, KOC(CH$_3$)$_3$, KC$_{10}$H$_8$, LiOH, LiOCH$_3$, LiOCH(CH$_3$)$_2$ and LiOCH(CH$_3$)$_3$, alkaline earth metal salts or quaternary ammonium salts are used. The added amount of the base is 0.5–100 equivalents, preferably 2–40 equivalents against the amine-phosphine-ruthenium complex or the phosphine-ruthenium complex.

Further, the hydrogen donating material means a lower alcohol such as methanol, ethanol, propanol, 2-propanol or butanol, and formic acid.

The amount of solvent is determined by the solubility and economies. For example, in case of 2-propanol, it is preferably used in 20–50 wt % although with respect to substrate the concentration, the reaction can be carried out at a low concentration of not more than 1% to a condition of nearly no solvent depending on the substrate.

In addition, although 1 atmospheric pressure as the pressure of hydrogen is sufficient owing to an extremely high activity of the present catalyst system, the range of 1–200 atmospheric pressure, preferably the range of 3–100 atmospheric pressure is desirable, it being possible to maintain a: high activity even at 50 atmospheric pressure or less considering the economies of the overall process.

With respect to the reaction temperature, although the reaction can be carried out preferably at 15° C. to 100° C. considering economies, it can be carried out at approximately room temperature of 25–40° C. However, in the invention it is characterized that the reaction proceeds even at low temperatures of −30–0° C. Although the reaction time varies according to reaction conditions such as a reaction substrate concentration, temperature and pressure, the reaction is completed within a few minutes to tens of hours. The examples specifically illustrates thereabout.

Further, although the optically active diphosphine compound in an optically active ruthenium complex represented by the general formula (1) or the general formula (2) can be obtained either in (+)-forms or (−)-forms, the indication thereof is omitted. Also, by selecting either of these (+)-forms or (−)-forms, an optically active alcohol with desirable absolute configuration can be obtained. Further, a combination of the absolute configuration of a diphosphine compound in the optically active ruthenium complex represented by the general formula (1) and the absolute configuration of the optically active diamine compound added, and a combination of the absolute configuration of the diphosphine compound in the optically active ruthenium complex represented by the general formula (2) and the absolute configuration of the diamine compound are important for obtaining a high optical yield, which being shown in the comparative examples described hereinafter.

EXAMPLES

Hydrogenation of carbonyl compounds in the invention can be carried out in either a batch type reaction or a continuous type reaction. In the following the invention is explained in more detail showing the examples. However, the invention is not limited by the following examples.

As representative examples, the optically active diphosphine and diamine compounds, which are used, are shown in the following.

Optically Active Diphosphine Compounds

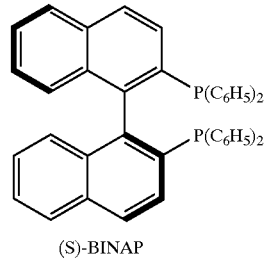

(S)-BINAP

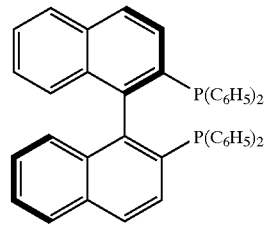

(R)-BINAP

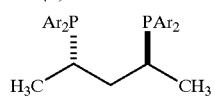

(S, S)-TolSKEWPHOS
Ar = p-CH$_3$C$_6$H$_4$
(S, S)-XylSKEWPHOS
Ar = 3′, 5′-(CH$_3$)$_2$C$_6$H$_3$

Optically active diamine compounds

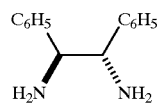

(S, S)-DPEN

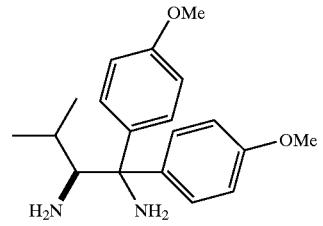

(S)-DAIPEN

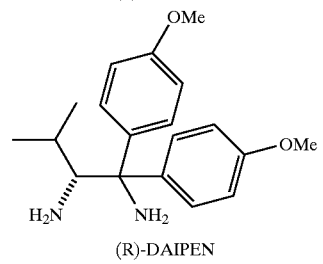

(R)-DAIPEN

-continued

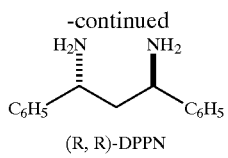

(R, R)-DPPN

Further, in the below examples all the reactions were carried out under an atmosphere of an inactive gas such as argon gas or nitrogen gas. Also, in terms of the solvents used in the reaction those dried and degassed were used. Hydrogenation of the carbonyl compounds was carried out in an autoclave by pressurizing hydrogen.

Further, the equipment below was used in the following measurements.

NMR: LA400 type apparatus (400 MHz)
 (manufactured by NIHON DENSHI Co., Ltd.)
 Internal standard: $^1$H-NMR Tetramethylsilane
 External standard: $^{31}$P-NMR 85% Phosphoric acid
Optical purity: Gas chromatography
 Chirasil-DEX CB (0.25 mm×25 m, DF=0.25 μm)
 (manufactured by CHROMPACK Co., Ltd.)
 High performance liquid chromatography
 CHIRACEL OD (0.46 cmØ×25 cm)
 (manufactured by DAISERU KAGAKU KOGYO Co., Ltd.)

Example 1

Synthesis of RuBr$_2$[(S,S)-Tolskewphos][(R)-daipen]

(1) Synthesis of Ru[(S,S)-Tolskewphos](methylallyl)$_2$ (S,S)-TolSKEWPHOS (568 mg, 1.14 mmol) and Ru(cycloocta-1,5-diene)(methylallyl)$_2$ (365 mg, 1.14 mmol) were placed in a 50 mL Schlenk tube replaced with argon. Then, 7 mL hexane was added to the mixture and stirred at 70° C. for 5 h. The insoluble material was filtered over a glass filter, and the solvent was evaporated.

(2) Synthesis of RuBr$_2$[(S,S)-Tolskewphos]

Ru[(S,S)-Tolskewphos](methylallyl)$_2$ complex (250 mg, 0.35 mmol) was dissolved in acetone 24 mL, 0.2M-HBr methanolic solution (3.5 mL, 0.7 mmol) was added, the mixture was degassed and stirred at room temperature for 30 min. After evaporation of the solvent the residue was used for the subsequent reaction without purification.

(3) Synthesis of RuBr$_2$[(S,S)-Tolskewphos][(R)-daipen]

(R)-DAIPEN (115 mg, 0.35 mmol) was added to RuBr$_2$[(S,S)-Tolskewphos] complex (316 mg, 0.35 mmol) and replaced with argon. Subsequently, dimethylformamide (14 mL) was added, the mixture was degassed, and stirred at room temperature overnight. After the reaction liquid was filtered through a glass filter packed with silicagel, the solvent was evaporated. The residue was crystallized from methylenechloride/isopropyl ether to give RuBr$_2$[(S,S)-Tolskewphos][(R)-daipen] 246 mg (66% yield).

$^1$H-NMR spectrum (C$_6$D$_6$): δ 6.65–7.88 (m, 24H), 5.24 (m, 1H), 5.18 (m, 1H), 3.95 (t, 1H), 3.38 (s, 3H), 3.20 (s, 3H), 2.24 (s, 3H), 2.17 (s, 3H), 2.05 (s, 3H), 2.04 (s, 3H), 1.71 (br, 1H), 1.39 (br, 2H), 1.07 (d, 3H), 1.05 (br, 1H), 0.53 (d, 3H), and the remaining 2H can not be attributed due to the overlap with other peaks.

Example 2

RuBr$_2$[(S,S)-Tolskewphos][(R)-daipen] (2.1 mg, 0.002 mmol) was placed in a 100 mL glass autoclave, replaced with argon; subsequently acetophenone (2.3 mL, 20 mmol) and 0.01M KOC(CH$_3$)$_3$/2-propanol solution (8 mL, 0.08 mmol) were added, the mixture was degassed and replaced with argon. Hydrogen was introduced to a pressure of 9 atm and the reaction was started (after 25 min, the conversion rate 86%). After the reaction liquid was stirred for 19 h, the reaction pressure was returned to a normal pressure, and the quantity and the optical purity of phenethyl alcohol, the product, were determined by gas chromatography on the reaction liquid. All the reaction substrate was consumed and the yield of the product was not less than 99%. Also, as for the obtained phenethyl alcohol, (R)-product was formed in 93.8% ee.

Comparative Example 1

Except for using RuCl$_2$[(R)-binap][(R)-daipen] instead of RuBr$_2$[(S,S)-Tolskewphos][(R)-daipen] as the catalyst, hydrogenation of acetophenone was carried out in the same way as Example 2 to give the product of phenethyl alcohol. The yield of the product was 99% or higher and (R)-product was formed in 85.0% ee.

Comparative Example 2

Except for using RuBr$_2$[(S,S)-Tolskewphos][(S)-daipen] instead of RuBr$_2$[(S,S)-Tolskewphos][(R)-daipen] as the catalyst, hydrogenation of acetophenone was carried out in the same way as Example 2 to give the product of phenethyl alcohol. The yield of the product was 99% or higher and (R)-product was formed in 90.2% ee.

Example 3

RuBr$_2$[(S,S)-Tolskewphos][(R)-daipen] (2.1 mg, 0.002 mmol) was placed in a 100 mL glass autoclave, replaced with argon, propiophenone (2.7 mL, 20 mmol), 0.01M KOC(CH$_3$)$_3$/2-propanol solution (8 mL, 0.08 mmol) were subsequently added, the mixture was degassed and replaced with argon. Hydrogen was introduced to a pressure of 9 atm and the reaction was started (after 20 min, the conversion rate 50%). After the reaction liquid was stirred for 19 h, the reaction pressure was returned to a normal pressure, and the quantity and the optical purity of the product of 1-phenyl-1-propanol were determined by gas chromatography on the reaction liquid. All the reaction substrate was consumed and the yield of the product was not less than 99%. Also, as for the obtained 1-phenyl-1-propanol, (R)-product was formed in 96.8% ee.

Comparative Example 3

Except for using RuCl$_2$[(R)-binap][(R)-daipen] instead of RuBr$_2$[(S,S)-Tolskewphos][(R)-daipen] as the catalyst, hydrogenation of propiophenone was carried out in the same way as Example 3 to give the product of 1-phenyl-1-propanol. The yield of the product was 99% or higher and (R)-product was formed in 91.5% ee.

Comparative Example 4

Except for using RuBr$_2$[(S,S)-Tolskewphos][(S)-daipen] instead of RuBr$_2$[(S,S)-Tolskewphos][(R)-daipen] as the catalyst, hydrogenation of propiophenone was carried out in the same way as Example 3 to give the product of 1-phenyl-1-propanol. The yield of the product was 99% or higher and (R)-product was formed in 93.2% ee.

Example 4

Synthesis of RuBr$_2$[(S,S)-Xylskewphos][(S,S)-dpen]

(1) Synthesis of Ru[(S,S)-Xylskewphos](methylallyl)$_2$ (S,S)-XylSKEWPHOS (301 mg, 0.545 mmol) and Ru(cycloocta-1,5-diene)(methylallyl)$_2$ (175 mg, 0.545 mmol) were placed in a 50 mL Schlenk tube replaced with argon. Then, 13 mL hexane was added to the mixture and stirred at 70° C. for 5 h. The insoluble material was filtered over a glass filter, and the solvent was evaporated.

(2) Synthesis of RuBr$_2$[(S,S)-Xylskewphos]

Ru[(S,S)-Xylskewphos](methylallyl)$_2$ complex (460 mg, 0.545 mmol) was dissolved in acetone (24 mL), 0.2M-HBr methanolic solution (5.45 mL, 1.090 mmol) was added, the mixture was degassed and stirred at room temperature for 40 min. After evaporation of the solvent, the residue was used for the subsequent reaction without purification.

(3) Synthesis of RuBr$_2$[(S,S)-Xylskewphos][(S,S)-dpen]

(S,S)-DPEN (177 mg, 0.834 mmol) was added to RuBr$_2$[(S,S)-Xylskewphos] complex (680 mg, 0.830 mmol) and replaced with argon. Subsequently, dimethylformamide (35 mL) was added to the mixture, degassed, and stirred at room temperature over night. After the reaction liquid was filtered through a glass filter packed with silicagel, the solvent was evaporated. The residue was crystallized from methylenechloride/isopropyl ether to give RuBr$_2$[(S,S)-Xylskewphos][(S,S)-dpen] 390 mg (34% yield).

$^{31}$P-NMR spectrum (C$_6$D$_6$): δ 66.01 (d, J=43 Hz), 42.85 (d, J=43 Hz).

Example 5

RuBr$_2$[(S,S)-Xylskewphos][(S,S)-dpen] (2.3 mg, 0.002 mmol) was placed in a 100 mL glass autoclave, replaced with argon, subsequently acetophenone (2.3 mL, 20 mmol) and 0.01M KOC(CH$_3$)$_3$/2-propanol solution (8 mL, 0.08 mmol) were added, degassed and replaced with argon. Hydrogen was introduced to a pressure of 9 atm and the reaction was started (after 25 min, the conversion rate 86%). After the reaction liquid was stirred for 19 h, the reaction pressure was returned to a normal pressure, and the quantity and the optical purity of the product of phenethyl alcohol were determined by gas chromatography on the reaction liquid. All the reaction substrate was consumed, and the yield of the product was not less than 99%. Also, as for the obtained phenethyl alcohol, (R)-product was formed in 95.0% ee.

Comparative Example 5

Except for using RuCl$_2$[(S)-binap][(S,S)-dpen] instead of RuBr$_2$[(S,S)-Xylskewphos][(S,S)-dpen] as the catalyst, hydrogenation of acetophenone was carried out in the same way as Example 5 to give the product of phenethyl alcohol. The yield of the product was 99% or higher and (S)-product was formed in 82.0% ee.

Example 6

Synthesis of RuBr$_2$[(S,S)-Xylskewphos][(R)-daipen]

(R)-DAIPEN (261 mg, 0.830 mmol) was added to RuBr$_2$[(S,S)-Xylskewphos] complex (679 mg, 0.830 mmol) obtained in Example 4 and replaced with argon. Subsequently, dimethylformamide (35 mL) was added to the mixture, the mixture was degassed, and stirred at room temperature over night. After the reaction the liquid was filtered through a glass filter packed with silicagel, the solvent was evaporated. The crude complex was washed with hexane to give RuBr$_2$[(S,S)-Xylskewphos][(R)-daipen] 647 mg (69%).

$^{31}$P-NMR spectrum (C$_6$D$_6$): δ 38.55 (d, J=39 Hz), 33.93 (d, J=39 Hz).

Example 7

RuBr$_2$[(S,S)-Xylskewphos][(R)-daipen] (2.3 mg, 0.002 mmol) was placed in a 100 mL glass autoclave, replaced with argon; subsequently acetophenone (2.3 mL, 20 mmol) and 0.01M KOC(CH$_3$)$_3$/2-propanol solution (8 mL, 0.08 mmol) were added, the mixture was degassed and replaced with argon. Hydrogen was introduced to a pressure of 9 atm and the reaction was started. After the reaction liquid was stirred for 50 min, the reaction pressure was returned to a normal pressure, and the quantity and the optical purity of the product of phenethyl alcohol were determined by gas chromatography of the reaction liquid. All the reaction substrate was consumed and the yield of the product was not less than 99%. Also, as for the obtained phenethyl alcohol, (R)-product was formed in 98.3% ee.

Comparative Example 6

Except for using RuCl$_2$[(R)-binap][(R)-daipen] instead of RuBr$_2$[(S,S)-Xylskewphos][(R)-daipen] as the catalyst, hydrogenation of acetophenone was carried out in the same way as Example 7 to give the product of phenethyl alcohol. The yield of the product was 99% or higher and (R)-product was formed in 85.0% ee.

Comparative Example 7

Except for using RuBr$_2$[(S,S)-Xylskewphos][(S)-daipen] instead of RuBr$_2$[(S,S)-Xylskewphos][(R)-daipen] as the catalyst, hydrogenation of acetophenone was carried out in the same way as Example 7 to give the product of phenethyl alcohol. The yield of the product was 99% or higher and (R)-product was formed in 82.6% ee.

Example 8

RuBr$_2$[(S,S)-Xylskewphos][(R)-daipen] (2,3 mg, 0.002 mmol) was placed in a 100 mL glass autoclave, replaced with argon subsequently 4-methyl-acetophenone (2.3 mL, 20 mmol) and 0.01M KOC(CH$_3$)$_3$/2-propanol solution (8 mL, 0.08 mmol) were added, the mixture was degassed and replaced with argon. Hydrogen was introduced to a pressure of 9 atm and the reaction was started (after 2 h, the conversion rate was 30%). After the reaction liquid was stirred for 22 h, the reaction pressure was returned to a normal pressure, and the quantity and the optical purity of the product of 4-methyl-phenethyl alcohol were determined by gas chromatography on the reaction liquid. All the reaction substrate was consumed, and the yield of the product was 99% or higher. Also, as for the obtained 4-methyl-phenethyl alcohol, (R)-product was formed in 91.6% ee.

Comparative Example 8

Except for using RuCl$_2$[(R)-binap][(R)-daipen] instead of RuBr$_2$[(S,S)-Xylskewphos][(R)-daipen] as the catalyst, hydrogenation of 4-methyl-acetophenone was carried out in the same way as Example 8 to give the product of 4-methyl-phenethyl alcohol. The yield of the product was 99% or higher and (R)-product was formed in 85.7% ee.

Comparative Example 9

Except for using RuBr$_2$[(S,S)-Xylskewphos][(S)-daipen] instead of RuBr$_2$[(S,S)-Xylskewphos][(R)-daipen] as the catalyst, hydrogenation of 4-methyl-acetophenone was carried out in the same way as Example 8 to give the product of 4-methyl-phenethyl alcohol. The yield of the product was 99% or higher and (R)-product was formed in 77.7% ee.

Example 9

RuBr$_2$[(S,S)-Xylskewphos][(R)-daipen] (2.3 mg, 0.002 mmol) was placed in a 100 mL glass autoclave, replaced with argon; subsequently propiophenone (2.3 mL, 20 mmol) and 0.01M KOC(CH$_3$)$_3$/2-propanol solution (8 mL, 0.08 mmol) were added, the mixture was degassed and replaced with argon. Hydrogen was introduced to a pressure of 9 atm and the reaction was started (after 2 h, the conversion rate 40%). After the reaction liquid was stirred for 20 h, the reaction pressure was returned to a normal pressure and the quantity and the optical purity of the product of 1-phenyl-1-propanol were determined by gas chromatography on the reaction liquid. All the reaction substrate was consumed and the yield of the product was 99% or higher. Also, as for the obtained 1-phenyl-1-propanol, (R)-product was formed in 100% ee.

Comparative Example 10

Except for using RuCl$_2$[(R)-binap][(R)-daipen] instead of RuBr$_2$[(S,S)-Xylskewphos][(R)-daipen] as the catalyst, hydrogenation of propiophenone was carried out in the same way as Example 9 to give the product of 1-phenyl-1-propanol. The yield of the product was 99% or higher and (R)-product was formed in 91.5% ee.

Comparative Example 11

Except for using RuBr$_2$[(S,S)-Xylskewphos][(S)-daipen] instead of RuBr$_2$[(S,S)-Xylskewphos][(R)-daipen] as the catalyst, hydrogenation of propiophenone was carried out in the same way as Example 9 to give the product of 1-phenyl-1-propanol. The yield of the product was 99% or higher and (R)-product was formed in 88.7% ee.

Example 10

RuBr$_2$[(S,S)-Xylskewphos][(R)-daipen] (0.58 mg, 0.0005 mmol) and KOC(CH$_3$)$_3$ (22.45 mg, 0.2 mmol) was placed in a 150 mL SUS autoclave, and replaced with argon. Subsequently, acetophenone (5.8 mL, 50 mmol) and 2-propanol (20 mL) were added, the mixture was degassed and replaced with argon. Hydrogen was introduced to a pressure of 40 atm and the reaction was started. After the reaction liquid was stirred for 24 h, the reaction pressure was returned to a normal pressure and the quantity and the optical purity of the product of phenethyl alcohol were determined by gas chromatography on the reaction liquid. All the reaction substrate was consumed and the yield of the product was 99% or higher. Also, as for the obtained phenethyl alcohol, (R)-product was formed in 97.9% ee.

Example 11

Synthesis of RuBr$_2$[(S,S)-Xylskewphos][(R,R)-dppn]

(R,R)-DPPN [(R,R)-1,3-diphenyl-1,3-propanediamine] (116 mg, 0.514 mmol) was added to RuBr$_2$[(S,S)-Xylskewphos] complex (421 mg, 0.514 mmol) obtained in Example 4 and replaced with argon. Subsequently, dimethylformamide (22 mL) was added to the mixture, degassed, and stirred at room temperature over night. After the reaction liquid was filtered through a glass filter packed with silicagel, the solvent was evaporated. The crude complex was washed with hexane to give RuBr$_2$[(S,S)-Xylskewphos][(R,R)-dppn] 647 mg (69%).

Example 12

RuBr$_2$[(S,S)-Xylskewphos][(R,R)-dppn] (2.1 mg, 0.002 mmol) was placed in a 100 mL glass autoclave, replaced with argon. Subsequently, propiophenone (2.3 mL, 20 mmol) and 0.01M KOC(CH$_3$)$_3$/2-propanol solution (8 mL, 0.08 mmol) were added, and the mixture was degassed and replaced with argon. Hydrogen was introduced to a pressure of 9 atm and the reaction was started. After the reaction liquid was stirred for 21 h, the reaction pressure was returned to a normal pressure, and the quantity and the optical purity of the product of 1-phenyl-1-propanol were determined by gas chromatography on the reaction liquid. All the reaction substrate was consumed and the yield of the product was 99% or higher. Also, as for the obtained 1-phenyl-1-propanol, (R)-product was formed in 92.2% ee.

Example 13

RuBr$_2$[(S,S)-Xylskewphos][(R)-daipen] (5.8 mg, 0.005 mmol) was placed in a 100 mL glass autoclave, replaced with argon. Subsequently, 2-N,N-dimethylaminoacetophenone (1.63 g, 10 mmol) and 0.01M KOC(CH$_3$)$_3$/2-propanol solution (5 mL, 0.05 mmol) were added, the mixture was degassed and replaced with argon. Hydrogen was introduced to a pressure of 9 atm and the reaction was started. After the reaction liquid was stirred for 15 h, the reaction pressure was returned to a normal pressure, and the quantity and the optical purity of the product of 2-N,N-dimethylaminophenethyl alcohol were determined by gas chromatography. All the reaction substrate was consumed and the yield of the product was 99% or higher. Also, the obtained 2-N,N-dimethylaminophenethyl alcohol was formed in 96.7% ee.

Example 14

RuBr$_2$[(S,S)-Xylskewphos][(R)-daipen] (2.3 mg, 0.002 mmol) was placed in a 100 mL glass autoclave, replaced with argon. Subsequently, 2-acetylthiophene (2.16 mL, 20 mmol) and 0.01M KOC(CH$_3$)$_3$/2-propanol solution (8 mL, 0.08 mmol) were added, the mixture was degassed and replaced with argon. Hydrogen was introduced to a pressure of 9 atm and the reaction was started. After the reaction liquid was stirred for 22 h, the reaction pressure was returned to a normal pressure and the quantity and the optical purity of the product of 1-(2-thienyl)ethanol were determined by gas chromatography on the reaction liquid. The yield of the product was 85%. Also, as to the obtained 1-(2-thienyl)ethanol alcohol, (R)-product was formed in 95.5% ee.

Example 15

RuBr$_2$[(S,S)-Xylskewphos][(R)-daipen] (2.3 mg, 0.002 mmol) and KOC(CH$_3$)$_3$ (9 mg, 0.08 mmol) was placed in a 100 mL glass autoclave, replaced with argon. Subsequently, 2-acetylfuran (1.0 mL, 10 mmol) and 2-propanol (5 mL) were added, the mixture was degassed and replaced with argon. Hydrogen was introduced to a pressure of 9 atm and the reaction was started. After the reaction liquid was stirred for 17 h, the reaction pressure was returned to a normal pressure, and the quantity and the optical purity of the product of 1-(2-furyl)ethanol were determined by gas chromatography of the reaction liquid. All the reaction substrate was consumed and the yield of the product was 99% or higher. Also, as for the obtained 1-(2-furyl)ethanol, (R)-product was formed in 97.0% ee.

Example 16

RuBr$_2$[(S,S)-Xylskewphos][(R)-daipen] (1.15 mg, 0.010 mmol) and KOC(CH$_3$)$_3$ (45 mg, 0.4 mmol) was placed in a 100 mL glass autoclave, replaced with argon. Subsequently, 2-acetylpyridine (2.24 mL, 20 mmol), B[OCH(CH$_3$)$_2$]$_3$ (0.046 mL, 0.20 mmol) and 2-propanol (8 mL) were added, the mixture was degassed and replaced with argon. Hydrogen was introduced to a pressure of 9 atm and the reaction was started. After the reaction liquid was stirred for 22 h, the reaction pressure was returned to a normal pressure, and the quantity and the optical purity of the product of 1-(2-pyridiyl)ethanol were determined by high performance liquid chromatography of the reaction liquid. All the reaction substrate was consumed and the yield of the product was 99% or higher. Also, as for the obtained 1-(2-pyridiyl)ethanol, (R)-product was formed in 83.0% ee.

Example 17

RuBr$_2$[(S,S)-Xylskewphos][(R)-daipen] (2.3 mg, 0.002 mmol) was placed in a 100 mL glass autoclave, replaced with argon. Subsequently, cyclohexyl methyl ketone (2.74 mL, 20 mmol) and 0.01M KOC(CH$_3$)$_3$/2-propanol solution (8 mL, 0.08 mmol) were added, the mixture was degassed and replaced with argon. Hydrogen was introduced to a pressure of 9 atm and the reaction was started. After the reaction liquid was stirred for 17 h, the reaction pressure was returned to a normal pressure and the quantity and the optical purity of the product of 1-cyclohexyl ethanol were determined by high performance liquid chromatography on the reaction liquid. The yield of the product was 97.7%. Also, the obtained 1-cyclohexyl ethanol was reacted with (R)-MTPACl[(R)-(-)-α-methoxy-α-(trifluoromethyl) phenylacetylchloride] in the presence of a base to obtain the optical purity. The product was formed in the optical purity of 94.4% ee.

Example 18

RuBr$_2$[(S,S)-Xylskewphos][(R)-daipen] (2.3 mg, 0.002 mmol) was placed in a 100 mL glass autoclave, replaced with argon. Subsequently, benzylacetone (3.0 mL, 20 mmol) and 0.01M KOC(CH$_3$)$_3$/2-propanol solution (8 mL, 0.08 mmol) were added, the mixture was degassed and replaced with argon. Hydrogen was introduced to a pressure of 9 atm and the reaction was started. After the reaction liquid was stirred for 17.5 h, the reaction pressure was returned to a normal pressure, and the quantity and the optical purity of the product of 1-phenyl-3-butanol were determined by gas chromatography on the reaction liquid. The yield of the product was 99.3%. Also, the obtained 1-phenyl-3-butanol was formed in 53.1% ee.

Example 19

RuBr$_2$[(S,S)-Xylskewphos][(R)-daipen] (2.3 mg, 0.002 mmol) was placed in a 100 mL glass autoclave, replaced with argon. Subsequently, 4-methyl-3-penten-2-one (2.3 mL, 20 mmol) and 0.01M KOC(CH$_3$)$_3$/2-propanol solution (8 mL, 0.08 mmol) were added, degassed and replaced with argon. Hydrogen was introduced to a pressure of 9 atm and the reaction was started. After the reaction liquid was stirred for 21 h, the reaction pressure was returned to a normal pressure and the quantity and the optical purity of the product of 4-methyl-3-penten-2-ol were determined by gas chromatography of the reaction liquid. The yield of the product was 99.5%. Also, as for the obtained 4-methyl-3-penten-2-ol, (R)-product was formed in 90.5% ee.

Example 20

RuBr$_2$[(S,S)-Xylskewphos][(R)-daipen] (1.15 mg, 0.001 mmol) was placed in a 100 mL glass autoclave, replaced with argon. Subsequently, 2,2,2-trifluoroacetophenone (1.36 mL, 10 mmol) and 0.01M KOC(CH$_3$)$_3$/2-propanol solution (4 mL, 0.04 mmol) were added, degassed and replaced with argon. Hydrogen was introduced to a pressure of 9 atm and the reaction was started. After the reaction liquid was stirred for 19 h, the reaction pressure was returned to a normal pressure, and the quantity and the optical purity of the product of 2,2,2-trifluorophenethyl alcohol were determined by gas chromatography on the reaction liquid. The yield of the product was 95%. Also, as for the obtained 2,2,2-trifluorophenethyl alcohol, (R)-product was formed in 78.1% ee.

Example 21

RuBr$_2$[(S,S)-Tolskewphos]complex (1.5 mg, 0.002 mmol) obtained in Example 1 and (R)-DAIPEN (0.6 mg, 0.002 mmol) was placed in a 100 mL glass autoclave under argon. Acetophenone (2.3 mL, 20 mmol and 0.01M KOC(CH$_3$)$_3$/2-propanol solution (8 mL, 0.08 mmol) were added, degassed and replaced with argon. Hydrogen was introduced to a pressure of 9 atm and the reaction was started. After the reaction liquid was stirred for 29 h, the reaction pressure was returned to a normal pressure and the quantity and the optical purity of the product of phenethyl alcohol were determined by gas chromatography on the reaction liquid. All the reaction substrate was consumed and the yield of the product was 99% or higher. Also, as for the obtained phenethyl alcohol, (R)-product was formed in 92.1% ee.

Example 22

RuBr$_2$[(S,S)-Xylskewphos]complex (1.6 mg, 0.002 mmol) obtained in Example 4 and (S,S)-DPEN (0.4 mg, 0.002 mmol) was placed in a 100 mL glass autoclave under argon. Acetophenone (2.3 mL, 20 mmol) and 0.01M KOC(CH$_3$)$_3$/2-propanol solution (8 mL, 0.08 mmol) were added, degassed and replaced with argon. Hydrogen was introduced to a pressure of 9 atm and the reaction was started. After the reaction liquid was stirred for 24 h, the reaction pressure was returned to a normal pressure and the quantity and the optical purity of the product of phenethyl alcohol were determined by gas chromatography on the reaction liquid. All the reaction substrate was consumed and the yield on the product was 99% or higher. Also, as for the obtained phenethyl alcohol, (R)-product was formed in 93.7% ee.

Example 23

RuBr$_2$[(S,S)-Xylskewphos]complex (1.6 mg, 0.002 mmol) obtained in Example 4 and (R)-DAIPEN (0.6 mg, 0.002 mmol) was placed in a 100 mL glass autoclave under argon, acetophenone (2.3 mL, 20 mmol) and 0.01M KOC(CH$_3$)$_3$/2-propanol solution (8 mL, 0.08 mmol) were added, degassed and replaced with argon Hydrogen was introduced to a pressure of 9 atm and the reaction was started. After the reaction liquid was stirred for 2 h, the reaction pressure was returned to a normal pressure, and the quantity and the optical purity of the product of phenethyl alcohol were determined by gas chromatography of the reaction liquid. All the reaction substrate was consumed and the yield of the product was not less than 99%. Also, as for the obtained phenethyl alcohol, (R)-product was formed in 97.3% ee.

Example 24

RuBr$_2$[(S,S)-3-methyl-Xylskewphos][(S)-daipen] (2.3 mg, 0.002 mmol) was placed in a 100 mL glass autoclave, replaced with argon. Subsequently, acetophenone (2.3 mL, 20 mmol) and 0.01M KOC(CH$_3$)$_3$/2-propanol solution (8 mL, 0.08 mmol) were added, degassed and replaced with argon. Hydrogen was introduced to a pressure of 9 atm and the reaction was started. After the reaction liquid was stirred for 19 h, the reaction pressure was returned to a normal pressure and the quantity and the optical purity of the product of phenethyl alcohol were determined by gas chromatography on the reaction liquid. All the reaction substrate was consumed and the yield of the product was not less than 99%. Also, as for the obtained phenethyl alcohol, (R)-product was formed in 94.4% ee.

Example 25

RuBr$_2$[(S,S)-3-methyl-Xylskewphos][(S)-daipen] (2.3 mg, 0.002 mmol) was placed in a 100 mL glass autoclave, replaced with argon. Subsequently, propiophenone (2.7 mL, 20 mmol) and 0.01M KOC(CH$_3$)$_3$/2-propanol solution (8 mL, 0.08 mmol) were added, degassed and replaced with argon. Hydrogen was introduced to a pressure of 9 atm and the reaction was started. After the reaction liquid was stirred for 19 h, the reaction pressure was returned to a normal pressure and the quantity and the optical purity of the product of 1-phenyl-1-propanol were determined by gas chromatography of the reaction liquid. All the reaction substrate was consumed and the yield of the product was 99% or higher. Also, as for the obtained 1-phenyl-1-propanol, (R)-product was formed in 95.7% ee.

Example 26

RuBr$_2$[(R,R)-1,3-diphenyl-1,3-bis(3,5-xylylphosphino) propane][(S)-daipen] (2.5 mg, 0.002 mmol) was placed in a 100 mL glass autoclave, replaced with argon. Subsequently, propiophenone (2.7 mL, 20 mmol) and 0.01M KOC(CH$_3$)$_3$/2-propanol solution (8 mL, 0.08 mmol) were added, degassed and replaced with argon. Hydrogen was introduced to a pressure of 9 atm and the reaction was started. After the reaction liquid was stirred for 24 h, the reaction pressure was returned to a normal pressure and the quantity and the optical purity of the product of 1-phenyl-1-propanol were determined by gas chromatography of the reaction liquid. All the reaction substrate was consumed and the yield of the product was 99% or higher. Also, as for the obtained 1-phenyl-1-propanol, (R)-product was formed in 81.6% ee.

Effect of the Invention

As shown above, the invention provides novel ruthenium complexes having as the. ligand an optically active diphosphine compound, which has asymmetry on carbon and is easy to synthesize and a process for preparing optically active alcoholic compounds using said complexes as the catalysts. The above novel ruthenium complexes according to the invention are excellent in the points of reactivity, enantioselectivity and the like in an asymmetric hydrogenation of carbonyl compounds compared with conventional ruthenium complex catalysts having as the ligand an optically active diphosphine compound having the axial chirality or the asymmetry on carbon and are industrially very useful.

The present invention is not to be limited in scope by examples provided, since the examples are intended as an illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim:

1. An optically active ruthenium complex represented by the general formula (1)

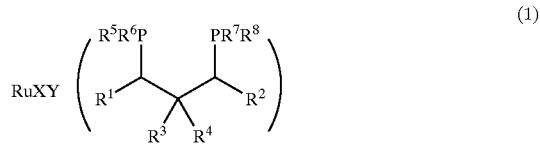

(1)

wherein X and Y, which can be identical to or different from each other, represent a hydrogen atom or an anion group, R$^1$ and R$^2$, which can be identical to or different from each other, represent a chain or cyclic hydrocarbon group of carbon number 1 to 20, which can be substituted, R$^3$ and R$^4$, which can be identical to or different from each other, represent a hydrogen atom or a hydrocarbon group of carbon number 1 to 3, and R$^5$, R$^6$, R$^7$ and R$^8$, which can be identical to or different from one another, represent a hydrocarbon group of carbon number 1 to 30, which can be substituted, with the proviso that when X and Y are bromine, R$^1$ and R$^2$ are a methyl group, and when R$^3$ and R$^4$ are a hydrogen atom, at least one of R$^5$, R$^6$, R$^7$ and R$^8$ is not a phenyl group.).

2. The optically active ruthenium complex according to claim 1 wherein R$^1$ and R$^2$ are a methyl group, R$^3$ and R$^4$, which can be identical to or different from each other, are a hydrogen atom or a hydrocarbon group of carbon number 1 to 3, and R$^5$, R$^6$, R$^7$ and R$^8$, which can be identical to or different from one another, are a phenyl, 4-tolyl or 3,5-xylyl group.

3. The optically active ruthenium complex according to claim 1 wherein R$^1$ and R$^2$ are a methyl group, R$^3$ and R$^4$ are a hydrogen atom, and R$^5$, R$^6$, R$^7$ and R$^8$, which are identical to one another, are a 4-tolyl or 3,5-xylyl group.

4. The optically active ruthenium complex according to claim 1 wherein R$^1$ and R$^2$ are a phenyl group, R$^3$ and R$^4$, which can be identical to or different from each other, are a hydrogen atom or a hydrocarbon group of carbon number 1 to 3, and R$^5$, R$^6$, R$^7$ and R$^8$, which are identical to one another, are a phenyl, 4-tolyl or 3,5-xylyl group.

5. A ruthenium complex represented by the general formula (2)

(2)

wherein X and Y, which can be identical to or different from each other, represent a hydrogen atom or an anion group, and A is a compound represented by the below general formula (3)

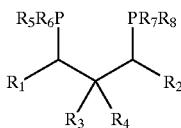

(3)

wherein $R^1$ and $R^2$, which can be identical to or different from each other, represent a chain or cyclic hydrocarbon group of carbon number 1 to 20, which can be substituted, $R^3$ and $R^4$, which can be identical to or different from each other, represent a hydrogen atom or a hydrocarbon group of carbon number 1 to 3, and $R^5$, $R^6$, $R^7$ and $R^8$, which can be identical to or different from one another, represent a hydrocarbon group of carbon number 1 to 30, which can be substituted.), and B is a compound represented by the below general formula (4)

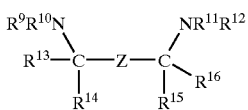

(4)

wherein $R^9$, $R^{10}$, $R^{11}$ and $R^{12}$, which can be identical to or different from one another, represent a hydrogen atom or a chain or cyclic hydrocarbon group of carbon number 1 to 30, which can be substituted, wherein at least one of these groups is a hydrogen atom, $R^{13}$, $R^{14}$, $R^{15}$ and $R^{16}$, which can be identical to or different from one another, represent a hydrogen atom or a chain or cyclic hydrocarbon group of carbon number 1 to 30, which can be substituted, and Z is a chain or cyclic hydrocarbon group of carbon number 1 to 10, which can be substituted, or a single bond, wherein the ruthenium complex represented by general formula (2) is not $RuCl_2$ ((S,S)-Skewphos)((S,S) diphenylethylenediamine or $RuCl_2$ ((S,S)-Skewphos)((R,R) diphenylethylenediamine.

6. The ruthenium complex according to claim 5 in which all of $R^5$, $R^6$, $R^7$ and $R^8$ are a phenyl group, wherein $R^{13}$ and $R^{15}$ are a hydrogen atom, $R^{14}$ and $R^{16}$ are a phenyl group, and when Z is a single bond, at least one of $R^9$, $R^{10}$, $R^{11}$ and $R^{12}$ is not a hydrogen atom.

7. The ruthenium complex according to claim 6 wherein all of $R^9$, $R^{10}$, $R^{11}$ and $R^{12}$ are a hydrogen atom, $R^{13}$ is a hydrogen atom, $R^{14}$ is an isopropyl group, $R^{15}$ and $R^{16}$ are 4-methoxyphenyl group, and Z is a single bond.

8. The ruthenium complex according to claim 5 wherein the compound A is a TolSKEWPHOS: 2,4-bis-(di-4-tolylphosphino)pentane, a XylSKEWPHOS: 2,4-bis-(di-3,5-xylylphosphino)pentane, 2,4-bis-(diphenylphosphino)-3-methylpentane, 2,4-bis-(di-4-tolylphosphino)-3-methylpentane, 2,4-bis-(di-3,5-xylylphosphino)-3-methylpentane, 1,3-bis-(diphenylphosphino)-1,3-diphenylpropane, 1,3-bis-(di-4-tolylphosphino)-1,3-diphenylpropane, 1,3-bis-(di-3,5-xylylphosphino)-1,3-diphenylpropane, 1,3-bis-(diphenylphosphino)-1,3-diphenyl-2-methylpropane, 1,3-bis-(di-4-tolylphosphino)-1,3-diphenyl-2-methylpropane or 1,3-bis-(di-3,5-xylylphosphino)-1,3-diphenyl-2-methylpropane, and the compound B is diphenylethylenediamine or 1-isopropyl-2,2-di(p-methoxyphenyl)ethylenediamine.

9. A process for preparing an alcoholic compound, wherein said process comprises a step of preparing the alcoholic compound by reducing a carbonyl compound with the reaction of hydrogen or a compound donating hydrogen in the presence of an optically active ruthenium complex represented by the general formula (1)

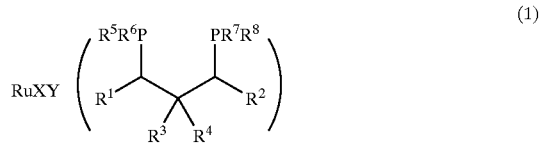

(1)

wherein X and Y, which can be identical to or different from each other, represent a hydrogen atom or an anion group, $R^1$ and $R^2$, which can be identical to or different from each other, represent a chain or cyclic hydrocarbon group of carbon number 1 to 20, which can be substituted, $R^3$ and $R^4$, which can be identical to or different from each other, represent a hydrogen atom or a hydrocarbon group of carbon number 1 to 3, and $R^5$, $R^6$, $R^7$ and $R^8$, which can be identical to or different from one another, represent a hydrocarbon group of carbon number 1 to 30, which an be substituted, with the proviso that when X and Y are bromine, $R^1$ and $R^2$ are a methyl group, and when $R^3$ and $R^4$ are a hydrogen atom, at least one of $R^5$, $R^6$, $R^7$ and $R^8$ does not represent a phenyl group, an optically active diamine compound represented by the general formula (4)

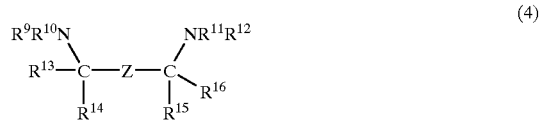

(4)

wherein $R^9$, $R^{10}$, $R^{11}$ and $R^{12}$, which can be identical to or different from one another, represent a hydrogen atom or a chain or cyclic hydrocarbon group of carbon number 1 to 30, which can be substituted, wherein at least one of these groups is a hydrogen atom, $R^{13}$, $R^{14}$, $R^{15}$ and $R^{16}$, which can be identical to or different from one another, represent a chain or cyclic hydrogen atom or a hydrocarbon group of carbon number 1 to 30, which can be substituted, , and Z is a chain or cyclic hydrocarbon group of carbon number 1 to 10, which can be substituted, or a single bond.), and a base (an alkaline metal or alkaline earth metal salt, or a quaternary ammonium salt).

10. The process according to claim 9, wherein $R^9$, $R^{10}$, $R^{11}$ and $R^{12}$ are a hydrogen atom, $R^{13}$ and $R^{15}$ are a hydrogen atom, $R^{14}$ and $R^{16}$ represent a phenyl group and Z represents a single bond, or $R^{13}$ represents a hydrogen atom, $R^{14}$ represents an isopropyl group, $R^{15}$ and $R^{16}$ represent 4-methoxyphenyl group and Z represents a single bond.

11. The process according to claim 9, wherein $R^1$ to $R^8$ are represented by the following a) to c):

a) $R^1$ and $R^2$ are a methyl group, $R^3$ and $R^4$, which can be identical to or different from each other, are a hydrogen atom or a hydrocarbon group of carbon number 1 to 3, and $R^5$, $R^6$, $R^7$ and $R^8$, which are one another identical, are a phenyl, 4-tolyl or 3,5-xylyl group;

b) $R^1$ and $R^2$ are a methyl group, $R^3$ and $R^4$ are a hydrogen atom, and $R^5$, $R^6$, $R^7$ and $R^8$, which are one another identical, are a 4-tolyl or 3,5-xylyl group; or c) $R^1$ and $R^2$ are a phenyl group, $R^3$ and $R^4$, which can be identical to or different from each other, represent a hydrogen atom or a hydrocarbon group of carbon number 1 to 3, and $R^5$, $R^6$, $R^7$ and $R^8$, which are one another identical, are a phenyl, 4-tolyl or 3,5-xylyl group.

12. A process for preparing an alcoholic compound, wherein said process comprises a step for preparing the alcoholic compound by reducing a carbonyl compound with the reaction of hydrogen or a compound donating hydrogen in the presence of an ruthenium complex represented by the general formula (2)

RuXYAB (2)

wherein X and Y, which can be identical to or different from each other, represent a hydrogen atom or an anion group, and A is a compound represented by the general formula (3)

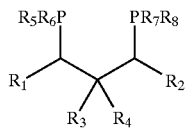

(3)

wherein $R^1$ and $R^2$, which can be identical to or different from each other, represent a chain or cyclic hydrocarbon group of carbon number 1 to 20, which can be substituted, $R^3$ and $R^4$, which can be identical to or different from each other, represent a hydrogen atom or a hydrocarbon group of carbon number 1 to 3, and $R^5$, $R^6$, $R^7$ and $R^8$, which can be identical to or different from one another, represent a hydrocarbon group of carbon number 1 to 30, which can be substituted, and B is a compound represented by the general formula (4)

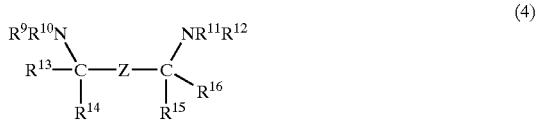

(4)

wherein $R^9$, $R^{10}$, $R^{11}$ and $R^{12}$, which can be identical to or different from one another, represent a hydrogen atom or a chain or cyclic hydrocarbon group of carbon number 1 to 30, which can be substituted, wherein at least one of these groups is a hydrogen atom, $R^{13}$, $R^{14}$, $R^{15}$ and $R^{16}$, which can be identical to or different from one another, represent a hydrogen atom or a chain or cyclic hydrocarbon group of carbon number 1 to 30, which can be substituted, and Z is a chain or cyclic hydrocarbon group of carbon number 1 to 10, which can be substituted, or a single bond a base (an alkaline metal or alkaline earth metal salt, or a quaternary ammonium salt), and wherein the ruthenium complex represented by general formula (2) is not RuCl$_2$ ((S,S)-Skewphos)((S,S) diphenylethylenediamine.

13. The process according to claim 12, wherein $R^1$ to $R^{16}$, the compound A and the compound B are represented by either of the following a) to c):

a) all of $R^5$, $R^6$, $R^7$ and $R^8$ are a phenyl group (with the proviso that when $R^{13}$ and $R^{15}$ are a hydrogen atom, $R^{14}$ and $R^{16}$ are a phenyl group, and when Z is a single bond, at least one of $R^9$, $R^{10}$, $R^{11}$ and $R^{12}$ is not a hydrogen atom);

b) all of $R^5$, $R^6$, $R^7$ and $R^8$ are a phenyl group, all of $R^9$, $R^{10}$, $R^{11}$ and $R^{12}$ are a hydrogen atom, $R^{13}$ is a hydrogen atom, additionally $R^{14}$ is an isopropyl group, $R^{15}$ and $R^{16}$ are a 4-methoxyphenyl group and Z is a single bond, or c) The compound A is a TolSKEWPHOS: 2,4-bis-(di-4-tolylphosphino)pentane, a XylSKEWPHOS: 2,4-bis-(di-3,5-xylylphosphino)pentane, 2,4-bis-(diphenylphosphino)-3-methylpentane, 2,4-bis-(di-4-tolylphosphino)-3-methylpentane, 2,4-bis-(di-3,5-xylylphosphino)-3-methylpentane, 1,3-bis-(diphenylphosphino)-1,3-diphenylpropane, 1,3-bis-(di-4-tolylphosphino)-1,3-diphenylpropane, 1,3-bis-(di-3,5-xylylphosphino)-1,3-diphenylpropane, 1,3-bis-(diphenylphosphino)-1,3-diphenyl-2-methylpropane, 1,3-bis-(di-4-tolylphosphino)-1,3-diphenyl-2-methylpropane or 1,3-bis-(di-3,5-xylylphosphino)-1,3-diphenyl-2-methylpropane, and the compound B is diphenylethylenediamine or 1-isopropyl-2,2-di(p-methoxyphenyl)ethylenediamine.

14. A process for preparing an optically active ruthenium complex represented by the general formula (1)

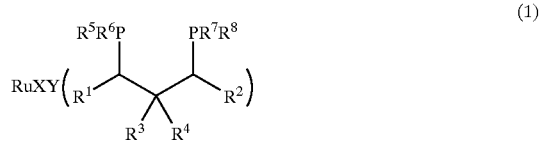

(1)

wherein X and Y, which can be identical to or different from each other, represent a hydrogen atom or an anion group, $R^1$ and $R^2$, which can be identical to or different from each other, represent a chain or cyclic hydrocarbon group of carbon number 1 to 20, which can be substituted, $R^3$ and $R^4$, which can be identical to or different from each other, represent a hydrogen atom or a hydrocarbon group of carbon number 1 to 3, and $R^5$, $R^6$, $R^7$ and $R^8$, which can be identical to or different from one another, represent a hydrocarbon group of carbon number 1 to 30, which can be substituted, with the proviso that when X and Y represent bromine, $R^1$ and $R^2$ are a methyl group, and when $R^3$ and $R^4$ are a hydrogen atom, at least one of $R^5$, $R^6$, $R^7$ and $R^8$ is not a phenyl group, wherein said process comprises a step for obtaining the compound represented by the above general formula (1) by reacting a compound represented by the general formula (5)

RuXY (5)

wherein X and Y, which can be identical to or different from each other, represent a hydrogen atom or an anion group, and a compound represented by the general formula (3)

(3)

wherein $R^1$ and $R^2$, which can be identical to or different from each other, represent a chain or cyclic hydrocarbon group of carbon number 1 to 20, which can be substituted, $R^3$ and $R^4$, which can be identical to or different from each other, represent a hydrogen atom or a hydrocarbon group of carbon number 1 to 3, and $R^5$, $R^6$, $R^7$ and $R^8$, which can be identical to or different from one another, represent a hydrocarbon group of carbon number 1 to 30, which can be substituted.

15. A process for preparing a ruthenium complex represented by the general formula (2)

   (2)

wherein X and Y, which can be identical to or different from each other, represent a hydrogen atom or an anion group, A is a compound represented by the below general formula (3)

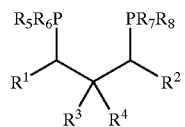   (3)

wherein $R^1$ and $R^2$, which can be identical to or different from each other, represent a chain or cyclic hydrocarbon group of carbon number 1 to 20, which can be substituted, $R^3$ and $R^4$, which can be identical to or different from each other, represent a hydrogen atom or a hydrocarbon group of carbon number 1 to 3, and $R^5$, $R^6$, $R^7$ and $R^8$, which can be identical to or different from one another, represent a hydrocarbon group of carbon number 1 to 30, which can be substituted, and B is a compound represented by the general formula (4)

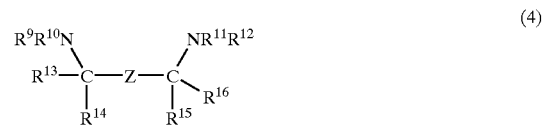   (4)

wherein $R^9$, $R^{10}$, $R^{11}$ and $R^{12}$, which can be identical to or different from one another, represent a hydrogen atom or a chain or cyclic hydrocarbon group of carbon number 1 to 30, which can be substituted, wherein at least one of these groups is a hydrogen atom, $R^{13}$, $R^{14}$, $R^{15}$ and $R^{16}$, which can be identical to or different from one another, represent a hydrogen atom or a chain or cyclic hydrocarbon group of carbon number 1 to 30, which can be substituted, and Z is a chain or cyclic hydrocarbon group of carbon number 1 to 10, which can be substituted, or a single bond, wherein said process comprises a step for obtaining the compound represented by the above general formula (2) by reacting a compound represented by the below general formula (1)

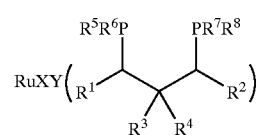   (1)

wherein each symbol has the same meaning as described above and the above compound B.

* * * * *